[12] United States Patent
Wilkes et al.

(10) Patent No.: US 11,969,319 B2
(45) Date of Patent: Apr. 30, 2024

(54) REDUCED-PRESSURE, COMPRESSION SYSTEMS AND APPARATUSES FOR USE ON A CURVED BODY PART

(71) Applicant: KCI Licensing, Inc., San Antonio, TX (US)

(72) Inventors: Robert Peyton Wilkes, San Antonio, TX (US); Justin Alexander Long, Lago Vista, TX (US); Richard Marvin Kazala, Jr., San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 674 days.

(21) Appl. No.: 17/062,382

(22) Filed: Oct. 2, 2020

(65) Prior Publication Data
US 2021/0022925 A1 Jan. 28, 2021

Related U.S. Application Data

(63) Continuation of application No. 15/864,937, filed on Jan. 8, 2018, now Pat. No. 11,020,277, which is a (Continued)

(51) Int. Cl.
A61F 13/06 (2006.01)
A61F 13/00 (2006.01)
(Continued)

(52) U.S. Cl.
CPC ...... A61F 13/022 (2013.01); A61F 13/00059 (2013.01); A61F 13/01017 (2024.01);
(Continued)

(58) Field of Classification Search
CPC .......... A61F 13/00059; A61F 13/00017; A61F 15/008; A61F 13/00029; A61F 13/00034;
(Continued)

(56) References Cited

U.S. PATENT DOCUMENTS 1,195,430 A 8/1916 Angier
1,355,846 A 10/1920 Rannells
(Continued)

FOREIGN PATENT DOCUMENTS

AU 550575 B2 3/1986
AU 745271 B2 3/2002
(Continued)

OTHER PUBLICATIONS

European Search Report for EP 09770665.9, dated Feb. 25, 2015.
(Continued)

Primary Examiner — Tarla R Patel

(57) ABSTRACT

A system for providing a force to a desired area on a curved body part of a person includes a dressing assembly shaped and configured to be placed on the desired area of the person, a releaseable circumferential member surrounding the curved body part that holds the dressing assembly against the desired area, a sealing subsystem for providing a fluid seal over the dressing assembly and the person's skin, and a reduced-pressure subsystem for providing a reduced pressure to the dressing assembly. When reduced pressure is supplied, the system generates the force against the desired area on the curved body part.

21 Claims, 12 Drawing Sheets

Related U.S. Application Data continuation of application No. 14/252,605, filed on Apr. 14, 2014, now Pat. No. 9,895,269, which is a continuation of application No. 13/253,711, filed on Oct. 5, 2011, now Pat. No. 8,722,959, which is a continuation of application No. 12/475,301, filed on May 29, 2009, now Pat. No. 8,129,580.

(60) Provisional application No. 61/144,067, filed on Jan. 12, 2009, provisional application No. 61/121,362, filed on Dec. 10, 2008, provisional application No. 61/057,810, filed on May 30, 2008, provisional application No. 61/057,803, filed on May 30, 2008, provisional application No. 61/057,805, filed on May 30, 2008, provisional application No. 61/057,802, filed on May 30, 2008, provisional application No. 61/057,798, filed on May 30, 2008, provisional application No. 61/057,808, filed on May 30, 2008, provisional application No. 61/057,807, filed on May 30, 2008, provisional application No. 61/057,800, filed on May 30, 2008, provisional application No. 61/057,797, filed on May 30, 2008.

(51) Int. Cl.

| | | |
|---|---|---|
| *A61F 13/01* | (2024.01) | |
| *A61F 13/02* | (2006.01) | |
| *A61F 13/0203* | (2024.01) | |
| *A61F 13/0206* | (2024.01) | |
| *A61F 13/05* | (2024.01) | |
| *A61F 15/00* | (2006.01) | |
| *A61H 1/00* | (2006.01) | |
| *A61L 15/60* | (2006.01) | |
| *A61M 1/00* | (2006.01) | |

(52) U.S. Cl.
CPC .. *A61F 13/01029* (2024.01); *A61F 13/01034* (2024.01); *A61F 13/01038* (2024.01); *A61F 13/0209* (2013.01); *A61F 13/0223* (2013.01); *A61F 13/0243* (2013.01); *A61F 13/0289* (2013.01); *A61F 13/05* (2024.01); *A61F 15/008* (2013.01); *A61H 1/008* (2013.01); *A61L 15/60* (2013.01); *A61M 1/71* (2021.05); *A61M 1/915* (2021.05); *H05K 999/99* (2013.01); *A61F 13/00* (2013.01); *A61F 2013/00131* (2013.01); *A61F 2013/00136* (2013.01); *A61F 2013/00174* (2013.01); *A61F 2013/00182* (2013.01); *A61F 2013/00246* (2013.01); *A61F 2013/0028* (2013.01); *A61F 2013/00536* (2013.01); *A61F 2013/0054* (2013.01); *A61F 2013/00748* (2013.01); *A61M 1/916* (2021.05); *A61M 2205/70* (2013.01); *A61M 2207/00* (2013.01); *A61M 2210/1007* (2013.01); *A61M 2210/1021* (2013.01); *Y10T 29/49* (2015.01); *Y10T 29/49826* (2015.01)

(58) Field of Classification Search
CPC ............ A61F 13/00038; A61F 13/0289; A61F 13/0216; A61F 13/0209; A61F 13/00068; A61F 13/022; A61F 13/0223; A61F 2013/00136; A61F 2013/00182; A61F 13/00; A61F 2013/00131; A61F 2013/0028; A61F 2013/00174; A61F 2013/0054; A61H 1/008; A61L 15/60; A61M 1/0088; A61M 2205/70; A61M 2207/00; Y10T 29/49826; Y10T 29/49

USPC ..... 602/41–48, 52–56, 58–60; 604/317, 358, 604/367, 369, 378, 381, 382, 383, 313; 424/447, 448, 443, 449

See application file for complete search history.

(56) References Cited

U.S. PATENT DOCUMENTS

| | | |
|---|---|---|
| 1,638,043 A | 8/1927 | Lee |
| 1,845,630 A | 2/1932 | Scholl |
| 2,452,345 A | 10/1948 | Ceyl |
| 2,547,758 A | 4/1951 | Kelling |
| 2,632,443 A | 3/1953 | Lesher |
| 2,682,873 A | 7/1954 | Evans et al. |
| 2,896,618 A | 7/1959 | Schaefer |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |
| 3,367,332 A | 2/1968 | Groves |
| 3,419,006 A | 12/1968 | Warwick |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,892,229 A | 7/1975 | Taylor et al. |
| 3,903,882 A | 9/1975 | Augurt |
| 3,969,561 A | 7/1976 | Marshall |
| 4,080,970 A | 3/1978 | Miller |
| 4,091,804 A | 5/1978 | Hasty |
| 4,096,853 A | 6/1978 | Weigand |
| 4,121,582 A | 10/1978 | Masso Remiro |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,430,998 A | 2/1984 | Harvey et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,572,814 A | 2/1986 | Naylor et al. |
| 4,605,399 A | 8/1986 | Weston et al. |
| 4,608,041 A | 8/1986 | Nielsen |
| 4,612,230 A | 9/1986 | Liland et al. |
| 4,640,688 A | 2/1987 | Hauser |
| 4,655,754 A | 4/1987 | Richmond et al. |
| 4,663,352 A | 5/1987 | Onofrj |
| 4,664,662 A | 5/1987 | Webster |
| 4,710,165 A | 12/1987 | McNeil et al. |
| 4,722,332 A | 2/1988 | Saggers |
| 4,727,868 A | 3/1988 | Szycher et al. |
| 4,733,659 A | 3/1988 | Edenbaum et al. |
| 4,743,232 A | 5/1988 | Kruger |
| 4,751,133 A | 6/1988 | Szycher et al. |

(56) References Cited

U.S. PATENT DOCUMENTS

| | | |
|---|---|---|
| 4,758,220 A | 7/1988 | Sundblom et al. |
| 4,770,490 A | 9/1988 | Gruenewald et al. |
| 4,787,888 A | 11/1988 | Fox |
| 4,795,435 A | 1/1989 | Steer |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,865,026 A | 9/1989 | Barrett |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,741 A | 3/1991 | Kalt |
| 5,018,515 A | 5/1991 | Gilman |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,306,798 A | 4/1994 | Horn et al. |
| 5,342,376 A | 8/1994 | Ruff |
| 5,344,415 A | 9/1994 | DeBusk et al. |
| 5,358,494 A | 10/1994 | Svedman |
| 5,376,067 A | 12/1994 | Daneshvar |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,653,244 A | 8/1997 | Shaw |
| 5,714,225 A | 2/1998 | Hansen et al. |
| 5,792,088 A | 8/1998 | Felder et al. |
| 5,844,013 A | 12/1998 | Kenndoff et al. |
| 5,866,249 A | 2/1999 | Yarusso et al. |
| 5,944,017 A | 8/1999 | Tweedle |
| 5,950,238 A | 9/1999 | Klein |
| 5,973,221 A | 10/1999 | Collyer et al. |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,162,960 A | 12/2000 | Klein |
| 6,176,868 B1 | 1/2001 | Detour |
| 6,213,840 B1 | 4/2001 | Han |
| 6,241,747 B1 | 6/2001 | Ruff |
| 6,270,910 B1 | 8/2001 | Jaeger et al. |
| 6,287,316 B1 | 9/2001 | Agarwal et al. |
| 6,320,093 B1 | 11/2001 | Augustine et al. |
| 6,345,623 B1 | 2/2002 | Heaton et al. |
| 6,361,397 B1 | 3/2002 | Mankovitz et al. |
| 6,420,622 B1 | 7/2002 | Johnston et al. |
| 6,426,931 B1 | 7/2002 | Parienti |
| 6,440,093 B1 | 8/2002 | McEwen et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,500,112 B1 | 12/2002 | Khouri |
| 6,528,697 B1 | 3/2003 | Knutson et al. |
| 6,553,998 B2 | 4/2003 | Heaton et al. |
| 6,566,576 B1 | 5/2003 | Komerska et al. |
| 6,648,862 B2 | 11/2003 | Watson |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,867,342 B2 | 3/2005 | Johnston et al. |
| D503,509 S | 4/2005 | Bell et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,070,584 B2 | 7/2006 | Johnson et al. |
| 7,090,647 B2 | 8/2006 | Mimura et al. |
| 7,135,007 B2 | 11/2006 | Scott et al. |
| 7,144,294 B2 | 12/2006 | Bell et al. |
| 7,195,624 B2 | 3/2007 | Lockwood et al. |
| 7,201,063 B2 | 4/2007 | Taylor |
| 7,201,263 B2 | 4/2007 | Osada et al. |
| 7,214,202 B1 | 5/2007 | Vogel et al. |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,455,681 B2 | 11/2008 | Wilke et al. |
| 7,504,549 B2 | 3/2009 | Castellani et al. |
| 7,520,872 B2 | 4/2009 | Biggie et al. |
| 7,532,953 B2 | 5/2009 | Vogel |
| 7,534,927 B2 | 5/2009 | Lockwood et al. |
| 7,569,742 B2 | 8/2009 | Haggstrom et al. |
| 7,699,831 B2 | 4/2010 | Bengtson et al. |
| 7,700,819 B2 | 4/2010 | Ambrosio et al. |
| 7,846,141 B2 | 12/2010 | Weston |
| 8,062,273 B2 | 11/2011 | Weston |
| 8,100,848 B2 | 1/2012 | Wilkes et al. |
| 8,129,580 B2 * | 3/2012 | Wilkes .................. A61H 1/008 424/443 |
| 8,202,261 B2 * | 6/2012 | Kazala, Jr. .............. A61L 15/60 604/304 |
| 8,216,198 B2 | 7/2012 | Heagle et al. |
| 8,241,261 B2 | 8/2012 | Randolph et al. |
| 8,251,979 B2 | 8/2012 | Malhi |
| 8,257,327 B2 | 9/2012 | Blott et al. |
| 8,398,614 B2 | 3/2013 | Blott et al. |
| 8,399,730 B2 | 3/2013 | Kazala, Jr. et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,641,691 B2 | 2/2014 | Fink et al. |
| 8,679,081 B2 | 3/2014 | Heagle et al. |
| 8,722,959 B2 * | 5/2014 | Wilkes ................ A61F 13/0209 424/443 |
| 8,834,451 B2 | 9/2014 | Blott et al. |
| 8,926,592 B2 | 1/2015 | Blott et al. |
| 9,017,302 B2 | 4/2015 | Vitaris et al. |
| 9,044,579 B2 | 6/2015 | Blott et al. |
| 9,095,468 B2 | 8/2015 | Kazala, Jr. et al. |
| 9,198,801 B2 | 12/2015 | Weston |
| 9,211,365 B2 | 12/2015 | Weston |
| 9,289,542 B2 | 3/2016 | Blott et al. |
| 9,456,928 B2 | 10/2016 | Haggstrom et al. |

(56) References Cited

U.S. PATENT DOCUMENTS

| | | | |
|---|---|---|---|
| 9,572,719 B2* | 2/2017 | Long | A61F 13/00034 |
| 9,750,641 B2 | 9/2017 | Kazala, Jr. et al. | |
| 9,895,269 B2* | 2/2018 | Wilkes | A61L 15/60 |
| 10,143,593 B2 | 12/2018 | Kazala, Jr. et al. | |
| 10,226,384 B2 | 3/2019 | Kazala, Jr. et al. | |
| 10,568,768 B2 | 2/2020 | Long et al. | |
| 11,020,277 B2* | 6/2021 | Wilkes | A61F 13/00029 |
| 2001/0029956 A1 | 10/2001 | Argenta et al. | |
| 2001/0043943 A1 | 11/2001 | Coffey | |
| 2002/0007014 A1 | 1/2002 | Hyde et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0040691 A1 | 2/2003 | Griesbach et al. | |
| 2003/0109816 A1 | 6/2003 | Lachenbruch et al. | |
| 2003/0139697 A1 | 7/2003 | Gilman | |
| 2003/0212359 A1 | 11/2003 | Butler | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0064111 A1 | 4/2004 | Lockwood et al. | |
| 2004/0064132 A1 | 4/2004 | Boehringer et al. | |
| 2004/0127836 A1 | 7/2004 | Sigurjonsson et al. | |
| 2004/0242119 A1 | 12/2004 | Francis | |
| 2004/0243073 A1 | 12/2004 | Lockwood et al. | |
| 2005/0059918 A1 | 3/2005 | Sigurjonsson et al. | |
| 2005/0070858 A1 | 3/2005 | Lockwood et al. | |
| 2005/0101940 A1 | 5/2005 | Radl et al. | |
| 2005/0142331 A1 | 6/2005 | Anderson et al. | |
| 2005/0209574 A1 | 9/2005 | Boehringer et al. | |
| 2005/0222544 A1 | 10/2005 | Weston | |
| 2005/0228329 A1 | 10/2005 | Boehringer et al. | |
| 2006/0041247 A1 | 2/2006 | Petrosenko et al. | |
| 2006/0064049 A1 | 3/2006 | Marcussen | |
| 2006/0079852 A1 | 4/2006 | Bubb et al. | |
| 2006/0149171 A1 | 7/2006 | Vogel et al. | |
| 2006/0173253 A1 | 8/2006 | Ganapathy et al. | |
| 2006/0189910 A1 | 8/2006 | Johnson et al. | |
| 2006/0213527 A1 | 9/2006 | Argenta et al. | |
| 2006/0264796 A1 | 11/2006 | Flick et al. | |
| 2007/0021697 A1 | 1/2007 | Ginther et al. | |
| 2007/0027414 A1 | 2/2007 | Hoffman et al. | |
| 2007/0032755 A1 | 2/2007 | Walsh | |
| 2007/0044801 A1 | 3/2007 | Mathis et al. | |
| 2007/0066946 A1 | 3/2007 | Haggstrom et al. | |
| 2007/0078366 A1 | 4/2007 | Haggstrom et al. | |
| 2007/0129707 A1 | 6/2007 | Blott et al. | |
| 2007/0135777 A1 | 6/2007 | Greene et al. | |
| 2007/0167884 A1 | 7/2007 | Mangrum et al. | |
| 2007/0185426 A1 | 8/2007 | Ambrosio et al. | |
| 2007/0185463 A1 | 8/2007 | Mulligan | |
| 2007/0219497 A1 | 9/2007 | Johnson et al. | |
| 2007/0219513 A1 | 9/2007 | Lina et al. | |
| 2007/0219532 A1 | 9/2007 | Karpowicz et al. | |
| 2007/0225663 A1 | 9/2007 | Watt et al. | |
| 2007/0255193 A1 | 11/2007 | Patel et al. | |
| 2008/0004549 A1 | 1/2008 | Anderson et al. | |
| 2008/0009812 A1 | 1/2008 | Riesinger | |
| 2008/0026023 A1 | 1/2008 | Tauer et al. | |
| 2008/0039763 A1 | 2/2008 | Sigurjonsson et al. | |
| 2008/0071207 A1 | 3/2008 | de Luis et al. | |
| 2008/0071214 A1 | 3/2008 | Locke et al. | |
| 2008/0076844 A1 | 3/2008 | Van Sumeren et al. | |
| 2008/0103462 A1 | 5/2008 | Wenzel et al. | |
| 2008/0103489 A1 | 5/2008 | Dahners | |
| 2008/0119802 A1 | 5/2008 | Riesinger | |
| 2009/0043268 A1 | 2/2009 | Eddy et al. | |
| 2009/0047855 A1 | 2/2009 | Seth et al. | |
| 2009/0125004 A1 | 5/2009 | Shen et al. | |
| 2009/0177051 A1 | 7/2009 | Arons et al. | |
| 2009/0204084 A1 | 8/2009 | Blott et al. | |
| 2009/0204085 A1 | 8/2009 | Biggie et al. | |
| 2009/0227968 A1 | 9/2009 | Vess | |
| 2009/0234307 A1 | 9/2009 | Vitaris | |
| 2009/0264807 A1 | 10/2009 | Haggstrom et al. | |
| 2009/0293887 A1 | 12/2009 | Wilkes et al. | |
| 2009/0299257 A1 | 12/2009 | Long et al. | |
| 2012/0220963 A1 | 8/2012 | Hunt et al. | |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| CA | 2468309 A1 | 7/2003 |
| CA | 2560068 A1 | 10/2005 |
| CA | 2651833 A1 | 11/2007 |
| CN | 101277734 A | 10/2008 |
| DE | 26 40 413 A1 | 3/1978 |
| DE | 39 07 522 C1 | 4/1990 |
| DE | 43 06 478 A1 | 9/1994 |
| DE | 29 504 378 U1 | 9/1995 |
| DE | 20 2006 007877 U1 | 7/2006 |
| DE | 102005007016 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0421465 A2 | 4/1991 |
| EP | 0424165 A1 | 4/1991 |
| EP | 0619105 A1 | 10/1994 |
| EP | 0691113 A1 | 1/1996 |
| EP | 0756854 A1 | 2/1997 |
| EP | 1018967 A1 | 7/2000 |
| EP | 2282788 B1 | 12/2016 |
| FR | 1163907 A | 10/1958 |
| FR | 2661821 A1 | 11/1991 |
| GB | 692578 A | 6/1953 |
| GB | 1574066 A | 9/1980 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| IN | 1545991 A | 11/2004 |
| JP | H08154964 A | 6/1996 |
| JP | H10356 A | 1/1998 |
| JP | 2000-189427 A | 7/2000 |
| JP | 2000210386 A | 8/2000 |
| JP | 2002-078730 A | 3/2002 |
| JP | 2003-116907 A | 4/2003 |
| JP | 2004-160220 A | 6/2004 |
| JP | 2006-141908 A | 6/2006 |
| JP | 2006219776 A | 8/2006 |
| JP | 2006239213 A | 9/2006 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 92/05755 A1 | 4/1992 |
| WO | 1993/000056 A1 | 1/1993 |
| WO | 93/009727 A1 | 5/1993 |
| WO | 199415562 A1 | 7/1994 |
| WO | 94/20041 A1 | 9/1994 |
| WO | 199420152 A1 | 9/1994 |
| WO | 1995/14451 A1 | 6/1995 |
| WO | 96/05873 A1 | 2/1996 |
| WO | 1997005838 A1 | 2/1997 |
| WO | 1997/11658 A1 | 4/1997 |
| WO | 97/18007 A1 | 5/1997 |
| WO | 99/01173 A1 | 1/1999 |
| WO | 99/13793 A1 | 3/1999 |
| WO | 0007653 A1 | 2/2000 |
| WO | 2000061206 A1 | 10/2000 |
| WO | 2001/02478 A1 | 1/2001 |
| WO | 01/034223 A1 | 5/2001 |
| WO | 01/85248 A1 | 11/2001 |
| WO | 2001/89431 A1 | 11/2001 |
| WO | 2002/20067 A2 | 3/2002 |

(56) References Cited

FOREIGN PATENT DOCUMENTS

| WO | 2002/083046 A1 | 10/2002 |
|---|---|---|
| WO | 2003017898 A1 | 3/2003 |
| WO | 03/057307 A1 | 7/2003 |
| WO | 2003/057071 A2 | 7/2003 |
| WO | 03070135 A2 | 8/2003 |
| WO | 2003077989 A1 | 9/2003 |
| WO | 2003/086262 A1 | 10/2003 |
| WO | 2003101385 A2 | 12/2003 |
| WO | 2004/047695 A1 | 6/2004 |
| WO | 2004/060413 A1 | 7/2004 |
| WO | 2005025447 A2 | 3/2005 |
| WO | 2005034797 A2 | 4/2005 |
| WO | 2005051461 A1 | 6/2005 |
| WO | 2005082435 A1 | 9/2005 |
| WO | 2005/091884 A2 | 10/2005 |
| WO | 2005/123170 A1 | 12/2005 |
| WO | 2006/012745 A1 | 2/2006 |
| WO | 2007030599 A2 | 3/2007 |
| WO | 2007031762 A1 | 3/2007 |
| WO | 2007033679 A2 | 3/2007 |
| WO | 2007/041642 A2 | 4/2007 |
| WO | 2007085396 A1 | 8/2007 |
| WO | 2007/120138 A2 | 10/2007 |
| WO | 2008013869 A2 | 1/2008 |
| WO | 2008013896 A2 | 1/2008 |
| WO | 2008/020209 A2 | 2/2008 |
| WO | 2008041926 A1 | 4/2008 |
| WO | 2008054312 A1 | 5/2008 |
| WO | 2008063281 A2 | 5/2008 |
| WO | 2008/104609 A1 | 9/2008 |
| WO | 2009019496 A2 | 2/2009 |
| WO | 2009/047524 A2 | 4/2009 |
| WO | 2009/071926 A1 | 6/2009 |

OTHER PUBLICATIONS

Laskin, et al.; "Minimally Invasive Total Knee Replacement Through a Mini-Midvastus Incision: An Outcome Study," Surgical Technology International XIII, 2004; 231-8.
A. Dee, "The successful management of a dehisced surgical wound with TNP following Femoropopliteal bypass", Journal of Wound Care, vol. 16, No. 1, Jan. 2007.
Ogazon, Use of Vacuum-Assisted Closure in the Treatment of Surgical Infection Sites Cir. Mar. 2006-Apr. 74(2): 107-13 (Spanish).
Timmenga, "The Effects of Mechanical Stress on Healing Skin Wounds: An Experimental Study in Rabbits Using Tissues Expansions," British Journal of Plastic Surgery 1991; 44(7): 514-519.
Cunningham "Development of in-vitro Model to Simulate Dermal Wound Bed Interaction with GranuFoam and Gauze Dressing under Sub Atmospheric Pressure" RPT 111-05-02, Device Implant Innovations 2006.
Delalleau, A., et al., "Characterization of the Mechanical Properties of Skin by Inverse Analysis Combined with the Indentation Test" Journal of Biomechanics, 2006; pp. 1603-1610.
Pailler-Mattei, C., "Caracte; Risation Me' Canique et Tribologizue de la Peau Humain In Vivo", 2004-31.
Khatyr, F., "Model of the Viscoelastic Behavior of Skin In Vivo and Study of Anisotropy", Skin Research and Technology 2004; pp. 96-103.
Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behavior of Biomedical Materials (2008), pp. 1-16.
Diridollou, "In vivo Model of the Mechanical Properties of the Human Skin under Suction", Skin Research and Technology, 2000; 6:214-221.
Woo, "Structural Model to Describe the Non-Linear Stress-Strain Behavior for Parallel-Fibered Collagenous Tissues," Journal of Biomechanical Engineering, Nov. 1989, vol. 111/361.

International Search Report and Written Opinion dated Oct. 20, 2009; PCT International Application No. PCT/US2009/045747.
International Search Report and Written Opinion dated Oct. 16, 2009; PCT International Application No. PCT/US2009/045752.
International Search Report and Written Opinion dated Oct. 14, 2009; PCT International Application No. PCT/US2009/045746.
International Search Report and Written Opinion dated Oct. 27, 2009; PCT International Application No. PCT/US2009/045744.
International Search Report and Written Opinion dated Oct. 26, 2009; PCT International Application No. PCT/US2009/045751.
International Search Report and Written Opinion dated Nov. 11, 2009; PCT International Application No. PCT/US2009/045754.
International Search Report and Written Opinion dated Oct. 21, 2009; PCT International Application No. PCT/US2009/045749.
International Search Report and Written Opinion dated Feb. 25, 2010; PCT International Application No. PCT/US2009/045750.
International Search Report and Written Opinion dated Mar. 12, 2010; PCT International Application No. PCT/US2009/045755.
Product Information for OptSiteTM dressing. Accessed Aug. 14, 2011.
International Search Report and Written Opinion dated Aug. 30, 2011 for PCT International Application No. PCT/US2011/034300.
International Search Report and Written Opinion dated Aug. 20, 2009; PCT International Application No. PCT/US2009/045743.
International Search Report and Written Opinion dated Nov. 12, 2009; PCT International Application No. PCT/US2009/045753.
Canadian Examiner's Report for Corresponding Application No. 2980359, dated Jul. 31, 2018.
A Prospective, Blinded, Randomized, Controlled Clinical Trial of Topical Negative Pressure Use in Skin Grafting, Elias Moisidis, Tim Heath, Catherine Boorer, Kevin Ho, Anand K. Deva, Sydney, Australia, From the Department of Plastic and Maxillofacial Surgery, Liverpool Hospital. Received for publication Mar. 25, 2003; revised Oct. 1, 2003.
The Vacuum Assisted Closure Device, a Method of Securing Skin Grafts and Improving Grafts Survival; Lynette A. Scherer, MD; Stephen Shiver, MD; Michael Chang, MD; J_ Wayne Meredith, MD; John T. Owings. MD; From the Departments of Surgery, University of California-Davis Medical Center, Sacramento (Ors. Sherer and Owings), and Wake Forest University Baptist Medical Center, Winston-Salem, NC (Ors. Shiver, Chang, and Meredith); Arch SurQNol 137, AuQ 2002; www.archsurQ.com.
Examination Report for corresponding EP 09770659.2, dated Sep. 4, 2013.
Extended European Search Report corresponding to Application No. 171645070, dated Jul. 18, 2017.
Extended European Search Report for corresponding Eurpean Application No. 12171212.9 dated Nov. 14, 2012.
European Search Report for EP 14182278.3 dated Jan. 7, 2015.
European Examination Report for corresponding EP09770663.4, dated Aug. 9, 2013.
Chintamani V.S. et al. : "Half Versus Full Vacuum Suction Drainage After Modified Radical Mastectomy for Breast Cancer—a Prospective Randomized Clinical Trial [ISRCTN24484328]", BMC Cancer, 2005, vol. 5, article 11; abstract.
Japanese Office Action corresponding to Application No. 2016104769, dated Mar. 7, 2017.
European Search Report for corresponding Application No. 16171527.1 dated Dec. 9, 2016.
Communication pursuant to Rule 114(2) EPC for corresponding EP Application 09770664.2, dated Aug. 22, 2013.
Canadian Office Action dated May 25, 2016, corresponding to Canada Application No. 2,725,945.
Mexican Office Action corresponding to Application No. MX/a/2010/013134, dated Oct. 26, 2017.
Indian Examination Report for corresponding Application No. 9029/DELNP/2010, dated Nov. 23, 2017.
Extended European Search Report for corresponding Application No. 161998968, dated Mar. 1, 2017.
Japanese Notice of Rejection Corresponding to Application No. 2017-235283, dated Aug. 6, 2019.
Extended European Search Report for corresponding Application No. 201963739, dated Jan. 1, 2021.

(56) References Cited

OTHER PUBLICATIONS

Japanese Notice of Rejection for corresponding Application No. 2020-005250, dated Oct. 27, 2020.
Chinese First Office Action for corresponding Application No. 202011083392.4, dated Aug. 2, 2021.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Office action for related U.S. Appl. No. 16/242,825, dated Oct. 27, 2021.
Office Action for related U.S. Appl. No. 16/278,638, dated Sep. 29, 2021.
Office Action for related U.S. Appl. No. 16/740,004, dated Oct. 4, 2021.

\* cited by examiner

REDUCED-PRESSURE, COMPRESSION SYSTEMS AND APPARATUSES FOR USE ON A CURVED BODY PART

RELATED APPLICATIONS

This application is a continuation of U.S. patent application Ser. No. 15/864,937, filed Jan. 8, 2018, which is a continuation of U.S. patent application Ser. No. 14/252,605, filed Apr. 14, 2014, which is a continuation of U.S. patent application Ser. No. 13/253,711 entitled "Reduced-Pressure, Compression Systems And Apparatuses For Use On A Curved Body Part", filed Oct. 5, 2011, now U.S. Pat. No. 8,722,959 which issued on May 13, 2014, which is a continuation of U.S. patent application Ser. No. 12/475,301, entitled "Reduced-Pressure, Compression Systems And Apparatuses For Use On A Curved Body Part," filed May 29, 2009, now U.S. Pat. No. 8,129,580 which issued on Mar. 6, 2012; which claims the benefit, under 35 USC § 119(e), of the filing of U.S. Provisional Patent Application Ser. No. 61/144,067, entitled "Reduced-Pressure, Compression System and Apparatus for use on a Joint," filed Jan. 12, 2009; which claims priority from U.S. Provisional Patent Application Ser. No. 61/121,362, entitled "Reduced-Pressure Wound treatment System Employing an Anisotropic Drape," filed Dec. 10, 2008; which claims priority from U.S. Provisional Patent Application Ser. No. 61/057,802, entitled "Reduced-Pressure Dressing Assembly For Use in Applying a Closing Force," filed May 30, 2008; which claims priority from U.S. Provisional Patent Application Ser. No. 61/057,803, entitled "Reduced-Pressure, Linear-Wound Treatment System," filed May 30, 2008; which claims priority from U.S. Provisional Patent Application Ser. No. 61/057,807, entitled "Reduced-pressure Surgical Wound Treatment System," filed May 30, 2008; which claims priority from U.S. Provisional Patent Application Ser. No. 61/057,808, entitled "See-Through, Reduced-Pressure Dressing," filed May 30, 2008; which claims priority from U.S. Provisional Patent Application Ser. No. 61/057,810, entitled "Reduced-Pressure, Compression System and Apparatus for use on a Joint," filed May 30, 2008; which claims priority from U.S. Provisional Patent Application Ser. No. 61/057,800, entitled "Reduced-Pressure, Compression System and Apparatus for use on a Curved Body Part," filed May 30, 2008; which claims priority from U.S. Provisional Patent Application Ser. No. 61/057,798, entitled "Dressing Assembly For Subcutaneous Wound treatment Using Reduce Pressure," filed May 30, 2008; which claims priority from U.S. Provisional Patent Application Ser. No. 61/057,797, entitled "Reduced-Pressure, Compression System and Apparatus for use on Breast Tissue," filed May 30, 2008; and which claims priority from U.S. Provisional Patent Application Ser. No. 61/057,805, entitled "Super-Absorbent, Reduced-Pressure Wound Dressing and System," filed May 30, 2008. All of the patent applications listed in this paragraph are hereby incorporated by reference for all purposes.

BACKGROUND

The present invention relates generally to medical treatment systems, and more particularly, to reduced-pressure wound treatment systems.

Physicians perform millions of surgical procedures each year around the world. Many of the procedures are performed as open surgery and an increasing number are performed using minimally invasive surgery, such as endoscopic, arthroscopic, and laparoscopic procedures. As one example, the American Society for Aesthetic Plastic Surgery reports that there were more than 450,000 liposuction procedures in the United States in 2007.

Surgical procedures involve acute wounds, e.g., an incision, in the skin and related tissue. In many instances, the incision is closed at the conclusion of the procedure using a mechanical apparatus, such as staples or suture, or closed using adhesives. Thereafter, the wound is often merely covered with a dry, sterile bandage. Of course, there is usually more disruption than just at the epidermis.

With many surgical procedures, particularly those done with minimally invasive techniques, much of the disruption or damage is below the epidermis, or at a subcutaneous level. Again, as one example, in one type of liposuction procedure, after the introduction of a tumescent fluid (saline, mild painkiller, and epinephrine), the surgeon will use a trocar and cannula with suction to remove fatty areas. In doing so, it is not uncommon to have subcutaneous voids and other tissue defects formed at tissue sites remote from the incision through which the cannula was placed or other incisions through which equipment was placed. The damaged tissue will need time and care to heal and poses a number of potential complications and risks including edema, seroma, hematoma, further bruising, and ecchymosis to name some.

BRIEF SUMMARY

According to one illustrative embodiment, a system for providing a force to a desired treatment area on a curved body part of a person includes a dressing assembly for placing on the desired treatment area of the person. The dressing assembly has a longitudinal portion with a first end and a second end. The dressing assembly also includes an interior surface member having a first surface and a second, inward-facing surface and a dressing bolster having a first surface and a second, inward-facing surface. The second, inward-facing surface of the dressing bolster is disposed against the first surface of the interior surface member. The system further includes a releaseable circumferential member coupled to the first end and second end of the dressing assembly, a sealing subsystem for providing a fluid seal over the dressing assembly, and a reduced-pressure subsystem for providing a reduced pressure to the dressing assembly.

According to one illustrative embodiment, a system for providing a force to a desired treatment area on a curved body part of a person includes a dressing assembly for placing on the desired treatment area of the person. The dressing assembly has a longitudinal portion with a first end and a second end. The dressing assembly includes a first material having a first surface and a second, inward-facing surface and a second material having a first surface and a second, inward-facing surface. The second, inward-facing surface of the first material is disposed against the first surface of the second material. The system further includes a releaseable circumferential member coupled to the first end and second end of the dressing assembly and a reduced-pressure subsystem for providing a reduced pressure to the dressing assembly.

According to one illustrative embodiment, a system for providing a compressive force to a desired treatment area on a person's torso includes a dressing assembly shaped and configured to be placed on at least a portion of the person's torso and a releasable circumferential connector for holding the dressing assembly against the torso. The circumferential connector and the dressing assembly include a circumferential member. The system further includes a sealing subsystem for providing a fluid seal over the dressing assembly and the person's epidermis and a reduced-pressure subsystem for providing reduced pressure to the dressing assembly whereupon the system is operable to generate a compressive force against at least a portion of the torso.

According to one illustrative embodiment, a system for providing a compressive force to a desired treatment area on a person's torso includes a dressing assembly for placing on the desired treatment area of the person. The dressing assembly includes a longitudinal portion with a first end and a second end, and a dressing bolster having a first surface and a second, inward-facing surface. The second, inward-facing surface of the dressing bolster is disposed against the first surface of the interior surface member. The dressing assembly further includes an envelope member surrounding the dressing bolster. The envelope member includes an interior surface member having a first surface and a second, inward-facing surface, and an exterior surface member having a first surface and a second, inward-facing surface. The second, inward-facing surface of the exterior surface member is disposed proximate the first surface of the dressing bolster. The dressing bolster is formed from a bolster material having a density greater than 25 kg/m3. the system further includes a releaseable circumferential member coupled to the first end and second end of the dressing assembly and a sealing subsystem for providing a fluid seal over the dressing assembly and the person's epidermis. The sealing subsystem includes an over-drape that extends over the exterior surface member, and a sealing apparatus for providing a fluid seal over a person's epidermis and the over-drape.

According to one illustrative embodiment, a method of manufacturing a system for providing a compressive force to a desired treatment area on a curved body part of a person includes the step of forming a dressing assembly shaped and configured to be placed on the desired treatment area of the person. The method further includes providing a releasable circumferential connector for holding the dressing assembly against the desired treatment area and providing a sealing subsystem for providing a fluid seal over the dressing assembly and the person's epidermis.

According to one illustrative embodiment, a method of providing a force to at least a portion of a curved body part of a person includes the steps of: deploying a dressing assembly on the curved body part. The dressing assembly includes an interior surface member for placing over the desired treatment area and having a first surface and a second, inward-facing surface and a dressing bolster having a first surface and a second, inward-facing surface. The second, inward-facing surface of the dressing bolster is disposed against the first surface of the interior surface member thereby sealing the dressing assembly to the curved body part. The method further includes providing reduced pressure to the dressing assembly. The dressing bolster has a first volume ($V_1$) at ambient pressure and a second volume ($V_2$) when under reduced pressure and $V_1 > V_2$.

According to one illustrative embodiment, a method for providing a force to a curved body part includes the step of: placing a dressing assembly against a desired area. The dressing assembly has a longitudinal portion with a first end and a second end. The method further includes releasably coupling the first end to the second end to hold the longitudinal portion of the dressing assembly against the patient in the desired treatment area; fluidly coupling a reduced-pressure source to the dressing assembly; and activating the reduced pressure source to provide reduced pressure to the dressing assembly. The dressing assembly is placed under reduced pressure and contracts to form a directed force.

Other objects, features, and advantages of the illustrative embodiments will become apparent with reference to the drawings and the detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

In the following detailed description of illustrative embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
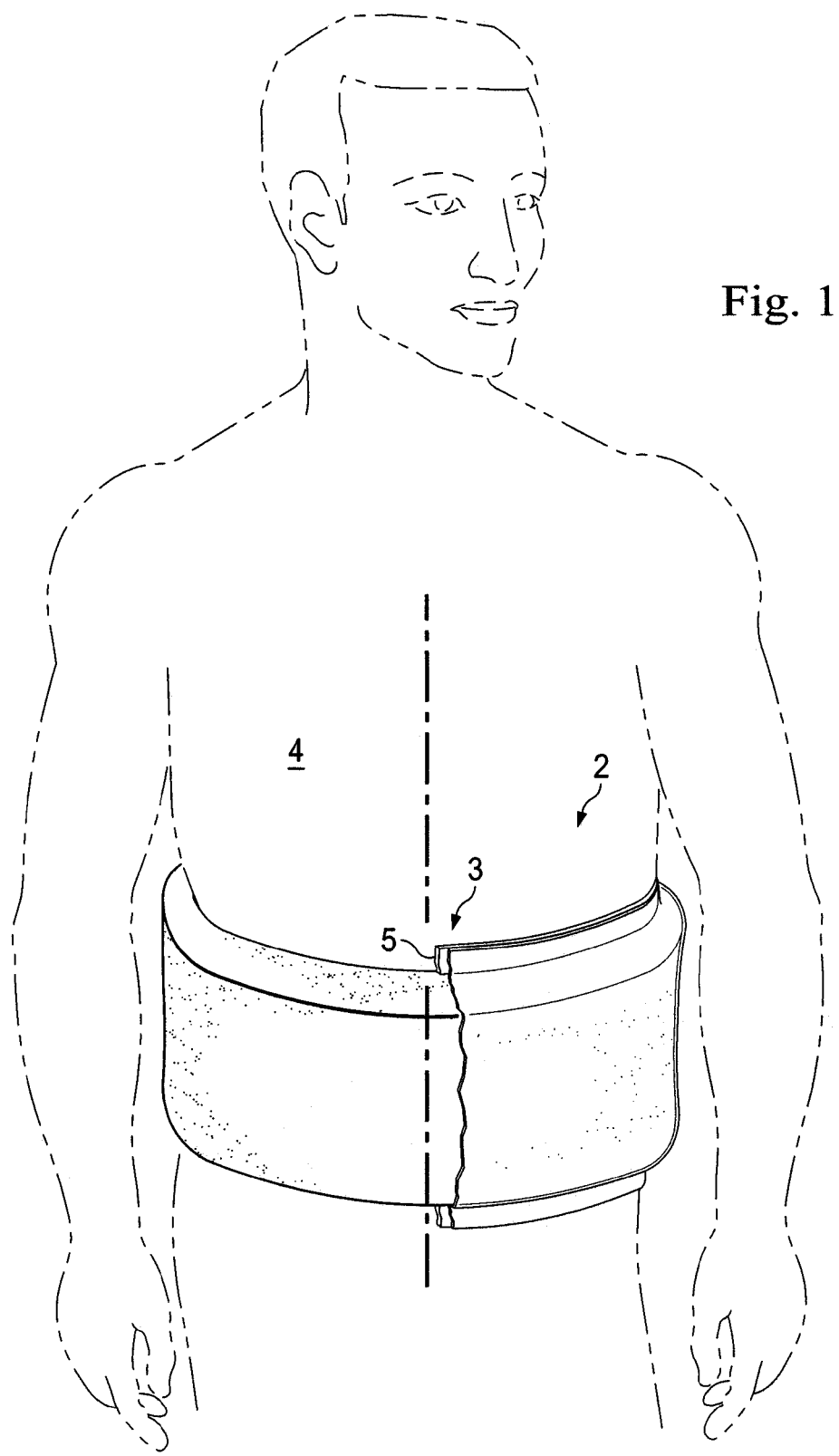
FIG. 1 is a schematic, perspective view of a portion of an illustrative embodiment of a reduced-pressure system shown on a person's torso.

Referring to FIG. 1, a system 2 for providing a force to a desired treatment area 3 on a person's torso 4 is shown. The system 2 may be applied in any situation in which support is desired for a given portion of a person's body such as the torso, an arm, leg, or other curved body part, but is described in the context of the torso 4. The system 2 may be applied when a force is desired for therapeutic reasons, such as providing a compression force, or inward force (or tangential force), and a lifting force, or upward force, to a desired treatment area while optionally removing fluids, such as exudates. The system 2 may be applied to treat subcutaneous tissue, treat surface tissue, or provide support. As used herein, subcutaneous means tissue at least as deep as the subcutaneous tissue, but also may include deeper tissues, including organs. Unless otherwise indicated, as used herein, "or" does not require mutual exclusivity. The system 2 may be applied simply when support is desired for cosmetic reasons or for any reason at all.

The system 2 allows support to be given to a portion of a person's body with relative ease, and the system 2 allows various sizes of body parts to be accommodated by a single system or apparatus thereby reducing the need for large inventories. When used with a wound, the system 2 may keep the wound dry, reduce dead space formation, improve perfusion, reduce seroma and hematoma formation, and reduce bruising and edema secondary to certain surgical procedures. The system 2 also provides comparative comfort for the patient or person using the system 2. The force developed by system 2 may be varied by varying the reduced pressure delivered to the system 2, and a feedback loop may be used to allow automated adjustments of reduced pressure to maintain a desired compressive force on a treatment site even as swelling increases or decreases.

Figure 2:
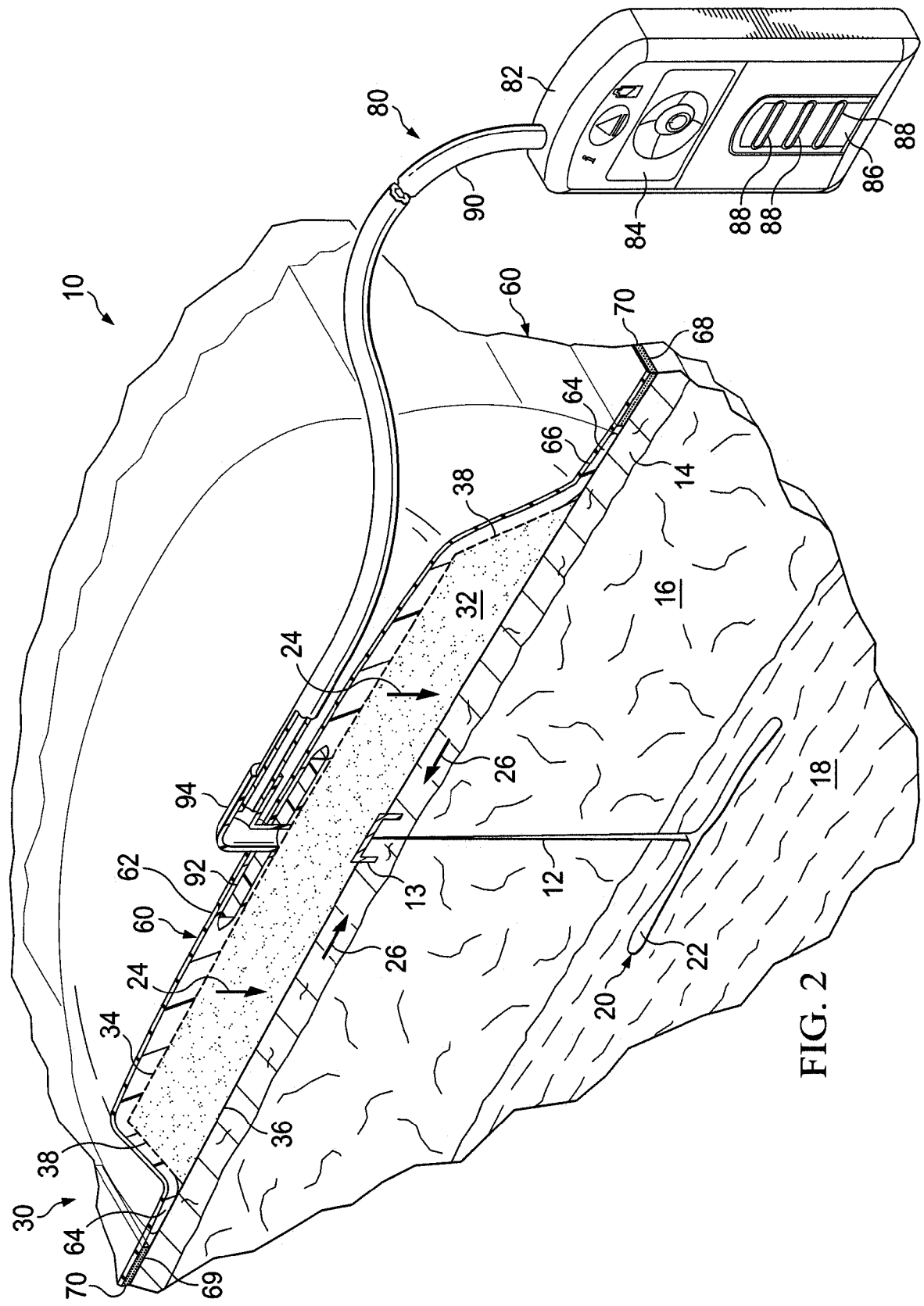
FIG. 2 is a schematic, perspective view, with a portion in cross section, of an illustrative embodiment of a reduced-pressure system shown over an incision and above undermined subcutaneous tissue.

Referring now to FIG. 2, an illustrative system 10 for treating undermined subcutaneous tissue in a peri-incisional region according to one illustrative embodiment is presented. The system 10 is shown in a peri-incisional region around an incision 12, which is through epidermis 14, or skin, and dermis 16 and reaches into a hypodermis, or subcutaneous tissue 18. The subcutaneous tissue 18 may include numerous tissue types such as fatty tissue or muscle. The undermined subcutaneous tissue site 20 is shown extending from incision 12 and includes, in this instance, subcutaneous defect or void 22. The undermined subcutaneous tissue 20 is often caused by surgical procedures such as liposuction. The undermined subcutaneous tissue 20 may include voids, such as the void 22, open spaces, and various defects that can be troublesome for a number of reasons. For example, the void 22 may allow fluids to build and that may result in edema. The term "fluid" as used herein generally refers to gas or liquid, but may also include any other flowable material, including but not limited to gels, colloids, and foams.

The incision 12 may be closed using any closing device such as staples, sutures, or adhesive, but is shown in this illustrative embodiment with a suture 13. The system 10 typically is for treating an area and, in particular, is typically for treating a subcutaneous tissue site 20 and the tissue around subcutaneous tissue 20, but the system 10 may also be used to treat the more limited area of the incision 12.

The system 10 includes a dressing assembly 30, which includes a shaped dressing bolster 32 (or dressing bolster), a sealing subsystem 60, and a reduced-pressure subsystem 80. The system 10 develops a net compressive force, represented by reference numerals 24, that is realized at the subcutaneous tissue 20. As described further below, the shaped dressing bolster 32 may be shaped and configured to allow the compressive force 24 to be distributed fairly evenly over the patient's epidermis 14 and beneath the epidermis 14. Otherwise, if there are areas of substantially increased force as compared to other areas, skin irritation may result. The system 10 may also be operable to develop an inward force (or closing force), i.e. towards an interior portion of dressing assembly 30. The inward force is represented by reference numerals 26. The inward force 26 may remain substantially within the plane of the epidermis 14. In other words, the inward force 26 operates mainly within the epidermis 14. In addition, the system 10 is operable to deliver reduced pressure to the incision 12. The reduced pressure may be realized at the level of the subcutaneous void 22 to help approximate—bring together—the tissues in that region as well as to help remove any air or any other fluids, e.g., exudates.

The dressing assembly 30 includes the shaped dressing bolster 32, which has a first side 34 and a second, inward (tissue-facing) side 36. The shaped dressing bolster 32 may be sized and shaped to substantially match the estimated area of undermined subcutaneous tissue 20 although a larger or smaller size may be used. The shaped dressing bolster 32 has a peripheral edge 38. The shaped dressing bolster 32 may be made of a number of different bolster materials. In one illustrative embodiment, the shaped dressing bolster 32 is made from a porous and permeable foam-like material and, more particularly, a reticulated, open-cell polyurethane or polyether foam that allows good permeability of wound fluids while under a reduced pressure. One such foam material that has been used is the VAC® Granufoam® material that is available from Kinetic Concepts, Inc. (KCI) of San Antonio, Texas Any material or combination of materials might be used for the bolster material provided that the bolster material is operable to distribute the reduced pressure and provide the desired forces.

The shaped dressing bolster 32 may be a manifold that is sized and shaped to distribute forces evenly and to distribute reduced pressure. The term "manifold" as used herein generally refers to a substance or structure that is provided to assist in applying reduced pressure to, delivering fluids to, or removing fluids from a tissue site. The manifold typically includes a plurality of flow channels or pathways that are interconnected to improve distribution of fluids provided to and removed from the tissue site around the manifold. The manifold may be a biocompatible material that is capable of being placed in contact with the tissue site and distributing reduced pressure to the tissue site. Examples of manifolds may include, for example, without limitation, devices that have structural elements arranged to form flow channels, such as, for example, cellular foam, open-cell foam, porous tissue collections, liquids, gels, and foams that include, or cure to include, flow channels. The manifold may be porous and may be made from foam, gauze, felted mat, or any other material suited to a particular biological application. Other embodiments might include "closed cells." In some situations, the manifold may also be used to distribute fluids such as medications, antibacterials, growth factors, and various solutions to the tissue site. Other layers may be included in or on the manifold, such as absorptive materials, wicking materials, hydrophobic materials, and hydrophilic materials.

The reticulated pores of the Granufoam® material, that are in the range from about 400 to 600 microns, are helpful in carrying out the manifolding function, but other materials may be used. The density of the medical bolster material, e.g., Granufoam® material, is typically in the range of about 1.3 lb/ft³-1.6 lb/ft³ (20.8 kg/m³-25.6 kg/m³). A material with a higher density (smaller pore size) than Granufoam® material may be desirable in some situations. For example, the Granufoam® material or similar material with a density greater than 1.6 lb/ft³ (25.6 kg/m³) may be used. As another example, the Granufoam® material or similar material with a density greater than 2.0 lb/ft³ (32 kg/m³) or 5.0 lb/ft³ (80.1 kg/m³) or even more may be used. The more dense the material is, the higher compressive force that may be generated for a given reduced pressure. If a foam with a density less than the tissue at the tissue site is used as the medical bolster material, a lifting force may be developed. In one illustrative embodiment, a portion, e.g., the edges, of the dressing assembly may exert a compressive force while another portion, e.g., a central portion, may provide a lifting force.

The bolster material may be a reticulated foam that is later felted to thickness of about one third (⅓) of the foam's original thickness. Among the many possible bolster materials, the following may be used: Granufoam® material or a Foamex® technical foam (www.foamex.com). In some instances it may be desirable to add ionic silver to the foam in a microbonding process or to add other substances to the bolster material such as antimicrobial agents. The bolster material may be isotropic or anisotropic depending on the exact orientation of the compressive forces 24 that are desired during the application of reduced pressure. The bolster material may also be a bio-absorbable material.

The sealing subsystem 60 includes an over-drape 62 (drape) or sealing member. The over-drape 62 may be an elastomeric material or may be any material that provides a fluid seal. "Fluid seal," or "seal," means a seal adequate to hold reduced pressure at a desired site given the particular reduced-pressure subsystem involved. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. As non-limiting examples, the over-drape 62 may be formed from materials that include a silicone, 3M Tegaderm® drape material, acrylic drape material such as one available from Avery, or an incise drape material.

The over-drape 62 may be coupled to the bolster 32. The coupling may occur in many ways. The over-drape 62 and the bolster 32 may be coupled using adhesives such as an acrylic adhesive, silicone adhesive, hydrogel, hydrocolloid, etc. The over-drape 62 and the bolster 32 might be bonded by heat bonding, ultrasonic bonding, and radio frequency bonding, etc. The coupling may occur in discrete patterns or more completely. Structural members might be added to the bond to make the over-drape 62 behave anisotropically in a desired direction, i.e. to make an anisotropic drape material. An anisotropic drape material helps the dressing assembly 30 to primarily move in a given direction, i.e. only about a certain axis or axes.

In the illustrative embodiment of FIG. 2, the over-drape 62 may be sized to extend beyond the peripheral edge 38 on an extremity 33 of the shaped dressing bolster 32 to form a drape extension 64. The drape extension 64 has a first surface 66 and a second, inward-facing surface 68. The over-drape 62 may be sealed against the epidermis 14 of the patient using a sealing apparatus or device 69 for providing a seal. The over-drape 62 and sealing apparatus 69 allow reduced pressure to be maintained at the tissue site by the reduced-pressure subsystem 80. The sealing apparatus 69 may take numerous forms, such as an adhesive 70; a sealing tape, or drape tape or strip; double-side drape tape; paste; hydrocolloid; hydrogel; or other sealing means. If a tape is used, it may be formed of the same material as the over-drape 62 with a pre-applied, pressure-sensitive adhesive. The pressure-sensitive adhesive 70 may be applied on the second surface 68 of the drape extension 64. The adhesive 70 provides a substantial fluid seal between the over-drape 62 and the epidermis 14 of the patient. The adhesive 70 may have removable strips covering the adhesive 70 that are removed before the drape extension 64 is applied to the patient's epidermis 14.

The reduced-pressure subsystem 80 includes a reduced-pressure source 82, which can take many different forms. The reduced-pressure source 82 provides a reduced pressure as a part of the system 10. The reduced-pressure source 82 may be any device for supplying a reduced pressure, such as a vacuum pump, wall suction, or other source. While the amount and nature of reduced pressure applied to a tissue site and shaped dressing bolster 32 will typically vary according to the application, the reduced pressure will typically be between −5 mm Hg and −500 mm Hg and more typically between −100 mm Hg and −300 mm Hg.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

In order to maximize patient mobility and ease, the reduced-pressure source 82 may be a battery-powered, single-use reduced-pressure generator. Such a reduced-pressure source 82 facilitates application in the operating room and provides mobility and convenience for the patient during the rehabilitation phase. The reduced-pressure source 82 has a battery compartment 84 and a canister region 86 with windows 88 providing a visual indication of the level of fluid within the canister 86. An interposed membrane filter, such as hydrophobic or oleophobic filter, might be interspersed between a reduced-pressure delivery conduit, or tubing, 90 and the reduced-pressure source 82.

For many procedures, it is believed that the patient would be directed to wear the system 10 for three to five days and may be directed to wear system 10 for 15 days or more. Still, the treatment time is a welcomed time period in contrast to treatment with conventional compressive garments, which are worn after many procedures today for up to six weeks. Accordingly, the battery life and/or power provisions may need to accommodate up to 15 days of operation. Other sources of reduced pressure may also be utilized such as V.A.C.® therapy unit, which is available from KCI of San Antonio, Texas, or a wall suction unit. The reduced-pressure source 82 may also be supplied by a portable mechanical device, such as a piston in a tube, depending on how much leakage there is with the fluid seal between the shaped dressing bolster 32 and the epidermis 14.

The reduced pressure developed by the reduced-pressure source 82 is delivered through the reduced-pressure delivery conduit 90 to a reduced-pressure interface 92, which may be an elbow port 94. In one illustrative embodiment, the port 94 is a TRAC® technology port available from KCI of San Antonio, Texas. The reduced-pressure interface 92 allows the reduced pressure to be delivered to the sealing subsystem 60 and realized within an interior portion of the sealing subsystem 60. In this illustrative embodiment, the port 94 extends through the over-drape 62 and into the shaped dressing bolster 32.

In operation, the system 10 may be applied in the operating room after a surgical procedure on the patient or at another time. The second surface 36 of the shaped dressing bolster 32 is placed against the patient's epidermis 14 with the shaped dressing bolster 32 over the undermined subcutaneous tissue site 20 and with a portion over the incision 12. The dressing assembly 30 may be sized for the typical application involved in the procedure performed by a healthcare provider. The dressing assembly 30 may be sized, shaped, and configured to work with different anatomical applications such as abdominal, chest, thighs, arms, etc.

If the over-drape 62 has not already been coupled (see other illustrative embodiments below) to the shaped dressing bolster 32, the over-drape 62 is then placed over the first surface 34 of the shaped dressing bolster 32 with an extra portion extending beyond the peripheral edge 38 to form the drape extension 64. The drape extension 64 can then be taped to the epidermis 14 (see 172 in FIG. 2) or an adhesive 70 (FIG. 1) used to form a fluid seal between the over-drape 62 and the patient's epidermis 14. The fluid seal need only be adequate to allow the system 10 to hold a reduced pressure on the treatment site. The reduced-pressure interface 92 and the reduced-pressure sources 82 are fluidly coupled using the reduced-pressure delivery conduit 90. The reduced-pressure source 82 may then be activated and reduced pressure delivered to the shaped dressing bolster 32.

As the pressure is reduced at the shaped dressing bolster 32, the shaped dressing bolster 32 compresses and contracts laterally and forms a semi-rigid substrate and, as a result, a number of beneficial forces and actions take place. The reduced pressure is transmitted further still through the shaped dressing bolster 32 so that reduced pressure is experienced at the patient's epidermis 14 at the incision 12. At least at the early stages of the healing process, the reduced pressure is realized through the incision 12 and into the subcutaneous tissue 20 and the reduction of pressure helps close defects, such as subcutaneous void 22, and generally provides stability to the area. The reduced pressure delivered to the shaped dressing bolster 32 also develops the compressive force 24 that again may provide stability and therapy. The compressive force 24 is more than just at the epidermis 14. The compressive force 24 extends down deeper and may be experienced at the level of subcutaneous tissue 20.

As the over-drape 62 and shaped dressing bolster 32 laterally contract under the influence of the reduced pressure, and as the downward force acts through the Poisson's ratio for the epidermis 14, an inward force 26 develops that may help hold a closing force on the incision 12 and may generally provide additional stability to the incision 12 or treatment site. The inward force 26 may rely in part on friction between the shaped dressing bolster 32 and the epidermis 14 to communicate the force to the epidermis 14 and may involve force transmission from the drape extension 64 to the epidermis 14 by way of the adhesive 70 or through friction if tape (172 in FIG. 2) is used. At the same time, the reduced pressure delivered to and through shaped dressing bolster 32 helps to remove any exudates or other fluids from the incision 12. The system 10 also allows the epidermis to be smoothed out with an even application of force—it contours and smoothes the epidermis 14. All these actions may improve healing of the incision 12 and the undermined subcutaneous tissue 20.

One operational concern is to avoid skin irritation in deploying and using the system 10. Accordingly, care is taken to avoid skin irritation, such as blistering of the patient's epidermis 14, that may be due to secondary shear, secondary strain or other effects. For this reason, the extremity 33 of the shaped dressing bolster 32 may be shaped to provide an even distribution of compressive forces. The extremity 33 is the outer, shaped portion of bolster 32 and the peripheral edge is generally the most outboard portion of the shaped dressing bolster 32 or the most outboard portion that interface with patient's epidermis. The extremity 33 may be a chamfered surface, but other shapes, e.g., an arcuate shape in system 110 (FIG. 2), may be used. Shapes that evenly distribute the resultant forces are desired. For comparison, when a dressing bolster with a square-edge is used, a "tent area" may form when the over-drape is applied over the dressing bolster and onto the patient's epidermis. The "tent area" is believed to contribute to issues with skin irritation. The "tent area" may be avoided by shaping the shaped bolster 32 or by attaching the over-drape to a side area of the dressing bolster.

The shaped edge, or extremity, of the shaped dressing bolster 32 allows a compressive force 24 to be developed without a big "edge effect"; that is, without causing shear or stress to rise to a level that causes skin irritation such as erythema or blistering. The shaped portion gradually distributes the force to avoid irritation. This way of carefully applying the forces to the epidermis 14 to avoid irritation is generally referred to as "evenly distributing" the compressive force 24, but is not strictly used in a literal sense. There may be some variation, but not enough to cause irritation of the epidermis 14. As another precaution against skin irritation, an inner layer might be added between the shaped dressing bolster 32 and the patient's epidermis 14 (see 857 in FIG. 11) or placed in other locations as explained in connection with other illustrative embodiments further below.

It may be desirable to apply the system 10 in the operating room and allow the system 10 to remain on the patient until adequate healing has taken place. In this regard, it may be desirable to form the over-drape 62, the shaped dressing bolster 32, and any other layers from see-through materials to allow the healthcare provider to gain visual cues about the healing of the incision 12 and the undermined subcutaneous tissue 20 without having to remove the dressing assembly 30.

Figure 3:
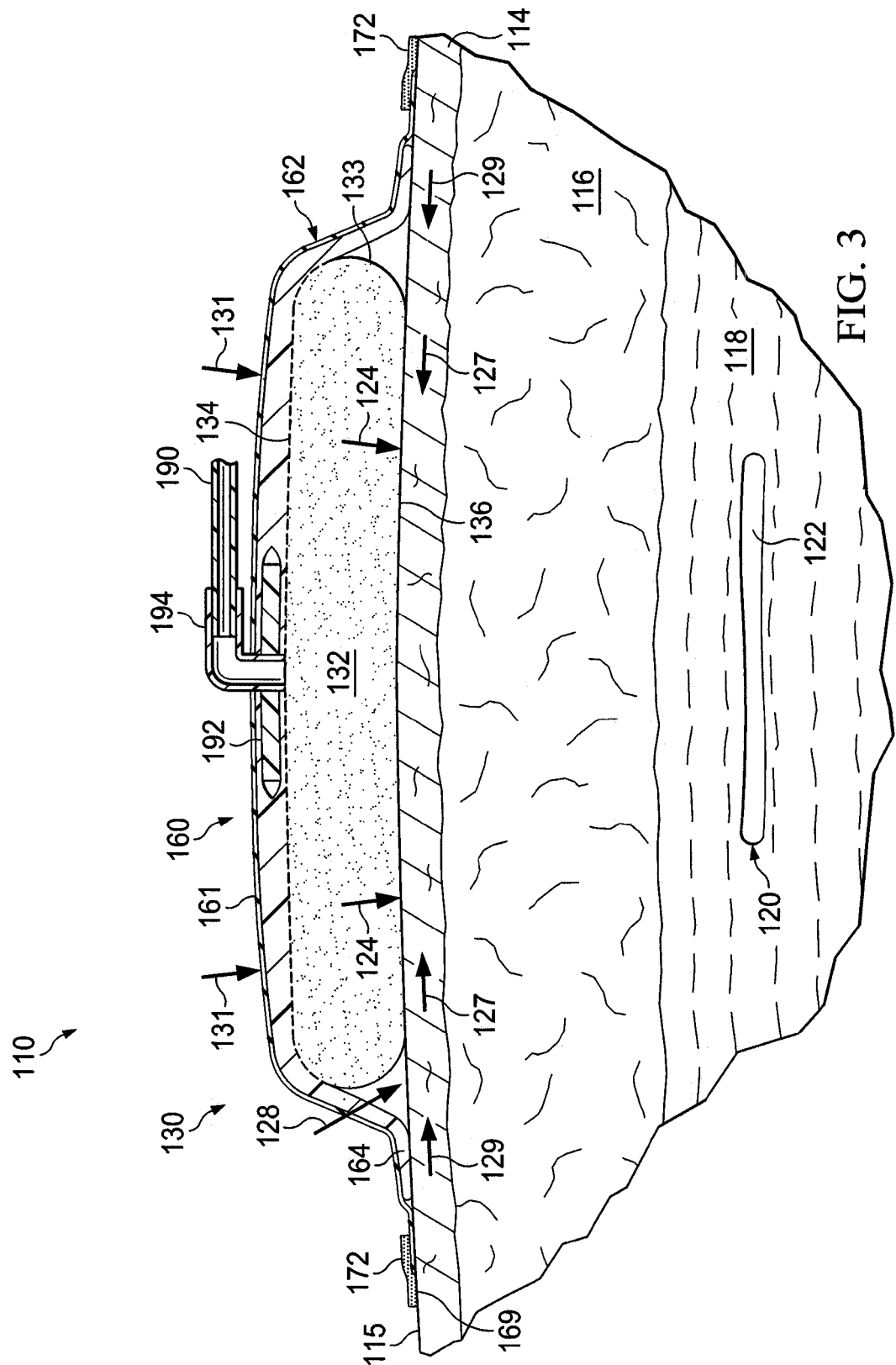
FIG. 3 is a cross-section of a portion of an illustrative embodiment of a reduced-pressure system shown on intact skin and over an area of undermined subcutaneous tissue.

Referring now to FIG. 3, another illustrative embodiment of a system 110 for treating undermined subcutaneous tissue in a patient is presented. The system 110 is analogous in most respects to the system 10 of FIG. 2 and analogous parts are generally indicated in this embodiment by indexing the numerals by 100. In this particular illustrative embodiment, the system 110 is placed over intact epidermis 115, i.e., there is no incision or other linear wound in this instance. There is, however, undermined subcutaneous tissue 120 including a subcutaneous void 122. The system 110 helps treat the undermined subcutaneous tissue 120 whether or not there is an incision.

The system 110 includes a dressing assembly 130 having a shaped dressing bolster 132. The shaped dressing bolster 132 has a first side 132 and a second, inward-facing side 136. While the shaped dressing bolster 32 of FIG. 2 was shown with a trapezoidal cross-section, a shaped dressing bolster 132 of FIG. 3 has a cross-section that is formed with an elliptical shape with an extremity 133 having radiused edges, or having an arcuate edge. The shaped dressing bolster 132 may be shaped with a double-beveled cross-section or other shape. As before, the shape of the shaped dressing bolster 132 is facilitates the even distribution of the compressive force to an extent that skin irritation is avoided during reduced pressure. In the illustrative embodiment of FIG. 3, a sealing apparatus 169 provides a fluid seal between an over-drape 162 and epidermis 114 of the patient. In this example, the sealing apparatus 169 is a sealing tape 172.

The system 110 includes a sealing subsystem 160 to provide a fluid seal over the shaped dressing bolster 132. A reduced-pressure delivery conduit 190 delivers reduced pressure to a reduced-pressure interface 192, e.g., a port 194, that is in fluid communication with an interior portion of the sealing subsystem 160.

In this illustrative embodiment, the ambient pressure provides a force 131 on a first surface 161 of the over-drape 162 and the contraction of the shaped dressing bolster 132 develops a compression force 124 to provide a net force that is experienced down into the skin and that reaches dermis 116 and may reach other subcutaneous levels 118. At the same time, a substantially in-plane force directed inward is developed. The inward force might be developed through two different mechanisms. First, an inward force 127 is an inward contraction force caused by the shaped dressing bolster 132 being compressed and as the shaped dressing bolster 132 compresses the shaped dressing bolster 132 is drawn inward. At the same time, as the reduced pressure is applied, the over-drape 162 is drawn into the area proximate the extremity 133 as suggested by arrow 128. Because a drape extension 164 is secured to the epidermis 114, the horizontal component of the resultant force 128 would pull the epidermis 114 inward as is suggested by the inward force 129.

Figure 4:
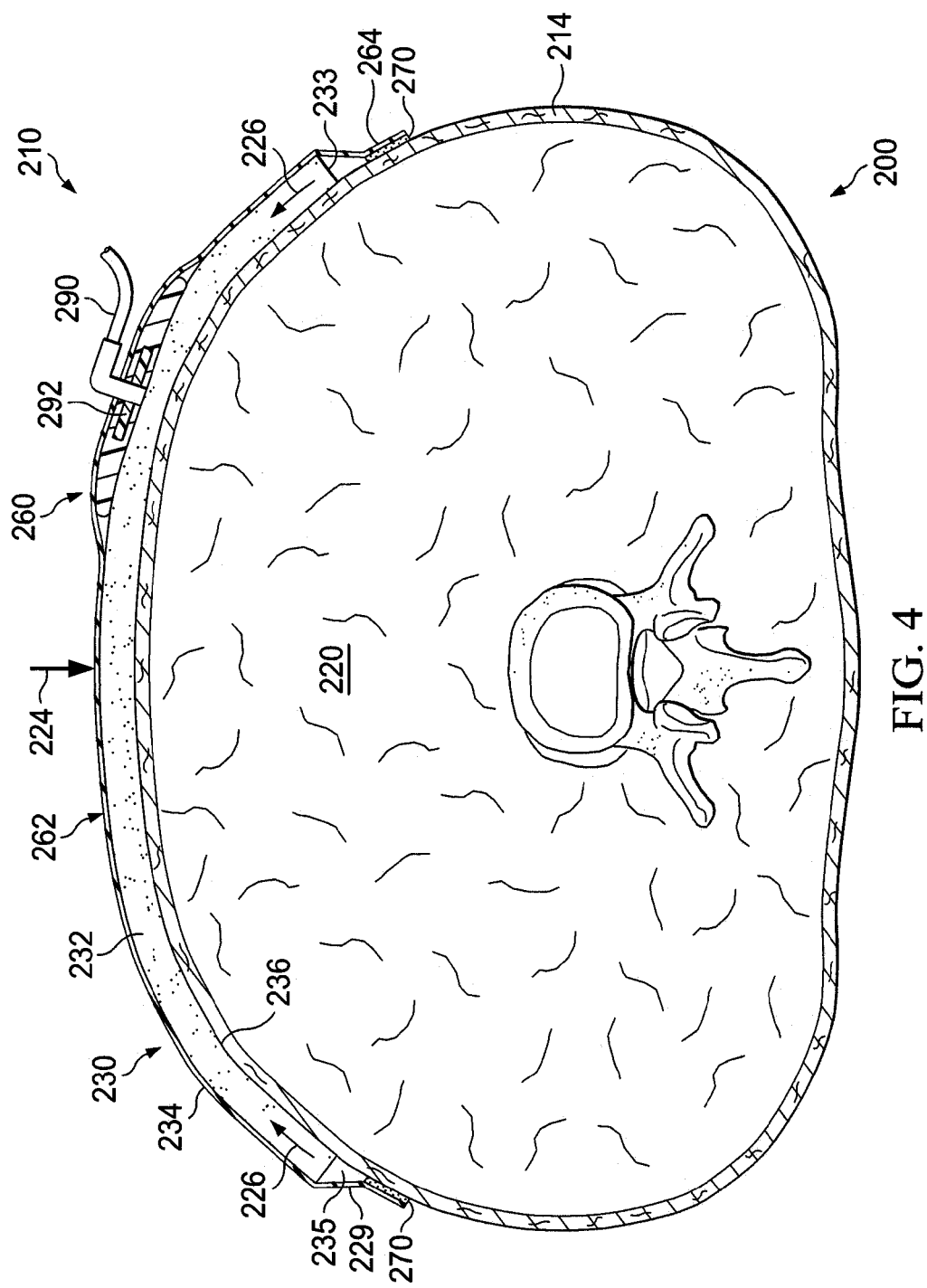
FIG. 4 is schematic, cross-section of a portion of an illustrative embodiment of a reduced-pressure system shown applied on a torso of a person.

Referring now to FIG. 4, a system 210 for treating a tissue site 220, e.g., an undermined subcutaneous tissue site, is shown on a curved body part 200, such as a patient's torso. The system 210 includes a dressing assembly 230 and a sealing subsystem 260. The dressing assembly 230 includes a shaped dressing bolster 232. The sealing subsystem 260 includes an over-drape 262 with an extension 264. The extension 264 may be secured to the patient's epidermis 214 by a sealing apparatus, such as an adhesive 270. A reduced-pressure source (not shown) provides reduced pressure to a reduced-pressure delivery conduit 290, which delivers the reduced pressure to a reduced-pressure interface 292.

The reduced-pressure interface 292 delivers the reduced pressure to the shaped dressing bolster 232. As the shaped dressing bolster 232 is compressed under the influence of reduced pressure, a net compressive force 224 is developed that is delivered to the tissue site 220. In this embodiment, an extremity 233 of the shaped dressing bolster 232 is formed with an orthogonal end. The over-drape 262 forms a "tent" area 229 around a void 235. Under reduced pressure, the over-drape 262 is pulled into the void 235 and a force is thereby applied that develops an inward contracting force 226.

In the system 210, the curvature of the shaped dressing bolster 232 also helps develop a compressive force. A first surface 234 of the shaped dressing bolster 232 has a greater surface area than the surface area of a second, inward-facing surface 236 of the shaped dressing bolster 232. Thus, under reduced pressure, this difference in surface areas also facilitates the development of a net compressive force 224.

Figure 5:
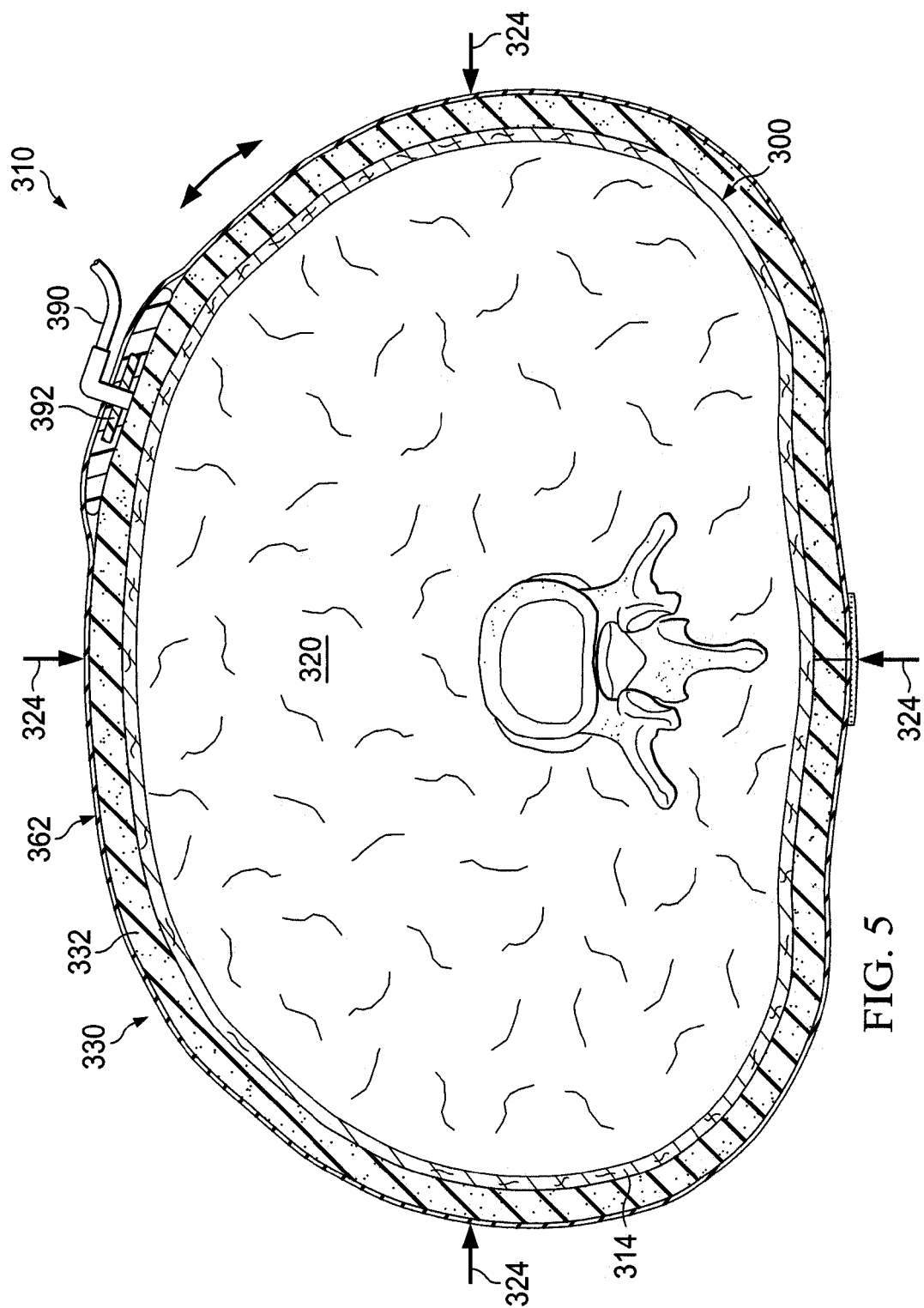
FIG. 5 is schematic, cross-section of a portion of an illustrative embodiment of a reduced-pressure system shown applied on a torso of a person.

Referring now to FIG. 5, an illustrative system 310 for treating a tissue site 320, e.g., an undermined subcutaneous tissue site, is presented. The system 310 is generally analogous in most respects to the system 210 of FIG. 4, and analogous parts are indicated by indexing the reference numerals of FIG. 4 by 100. The system 310 is applied to a curved body part 300, e.g., a patient's torso. The system 310 presents a completely circumferential dressing assembly 330 deployed proximate epidermis 314.

A dressing bolster 332 is disposed against the epidermis 314 and a drape, or an over-drape 362, is used to form a sealed area containing the dressing bolster 332. Reduced pressure is delivered through a reduced-pressure conduit 390 to a reduced-pressure interface 392. The reduced-pressure interface 392 delivers reduced pressure to the dressing bolster 332. Circumferential forces developed during the application of reduced pressure combine in the system 310 to develop inward compressive forces 324. The compressive forces can be higher than a flat or partial-torso application because there is no off-loading of force to the drape and to the skin.

Figure 6:
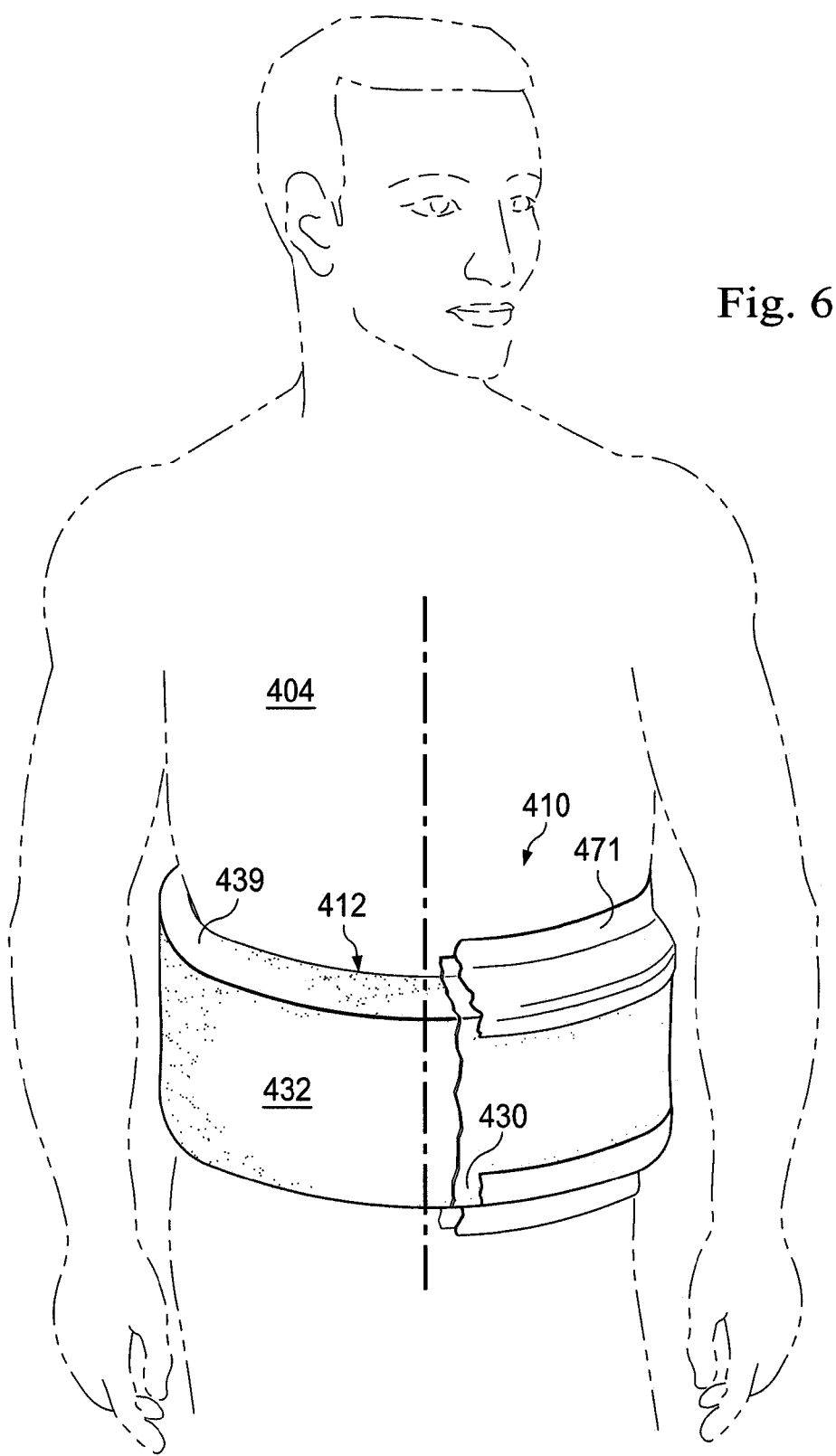
FIG. 6 is an anterior, schematic, perspective view of a portion of an illustrative embodiment of a reduced-pressure system shown on a torso.
Figure 7:
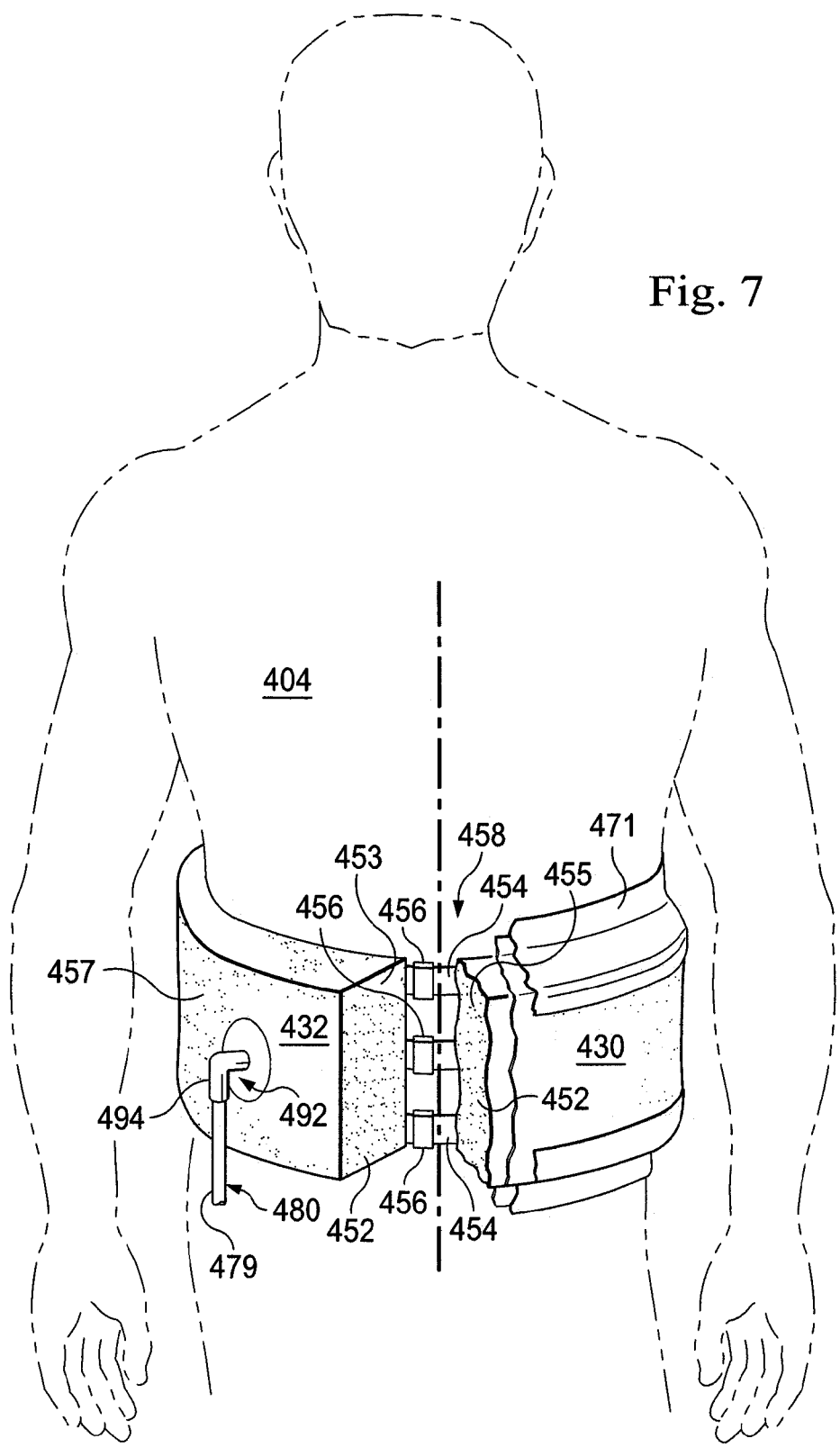
FIG. 7 is a posterior, schematic, perspective view of a portion of the illustrative system shown in FIG. 6.
Figure 8:
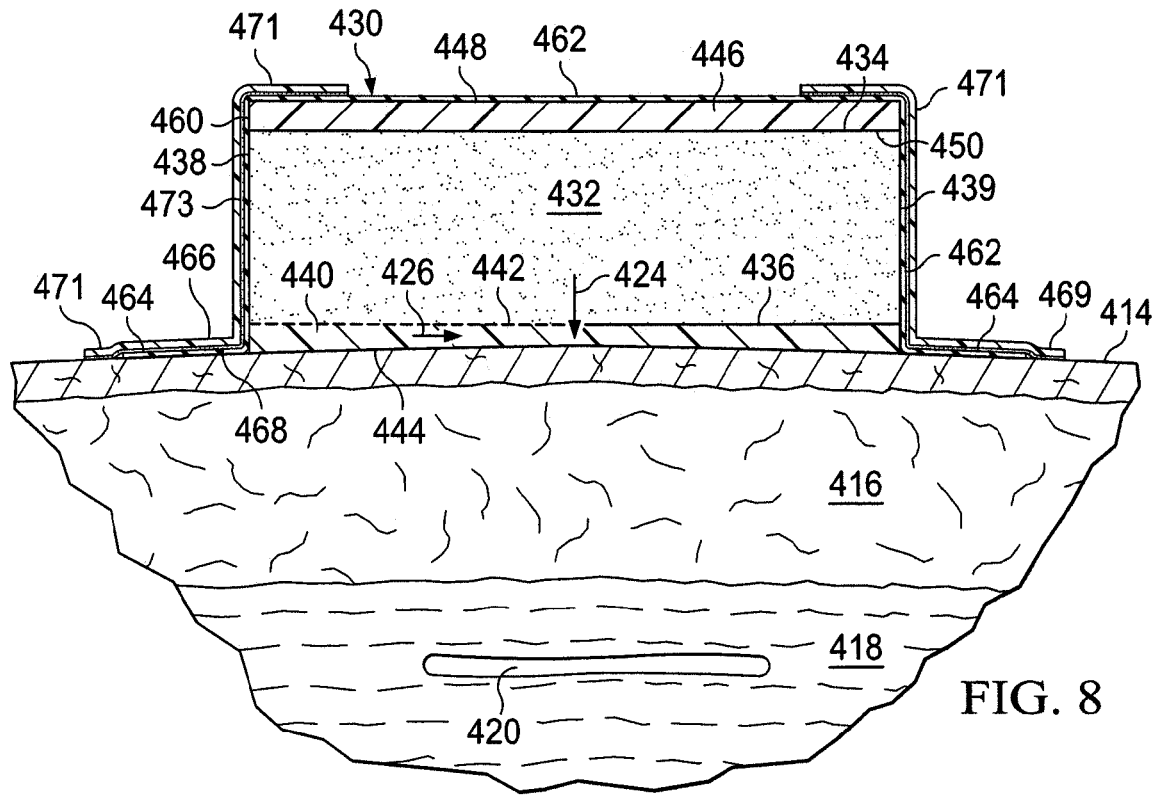
FIG. 8 is a schematic cross-section of a portion of an illustrative embodiment of a reduced-pressure, compression system.

Referring now to FIGS. 6-8, a system 410 for treating a treatment area 412 of a patient is presented. The treatment provided in this illustration is a force to the treatment area 412, which on the patient's torso 404. Treatment could also include removal of fluids at an incision or incisions. For this illustrative embodiment, the desired treatment area 412 is shown as the abdomen of the patient. If the patient has had, for example, tumescent liposuction, it may be desirable to use the system 410 to apply a compressive force realized at an incision or incisions, to apply a compressive force that is realized at the dermis 416 and at undermined subcutaneous tissue 420, to provide for the approximation of subcutaneous tissue 418 as well as stabilizing the tissue against sheer stress, and to remove any exiting fluids such as tumescent fluid or exudate. The system 410 includes a dressing assembly 430 that extends circumferentially at least partially around the torso 404 of the patient. The dressing assembly 430 includes a dressing bolster 432, which has a first peripheral edge 439.

As shown clearly in FIG. 8, the dressing bolster 432 has a first surface 434 and a second, inward-facing (or tissue-facing) surface 436. The dressing bolster 432 distributes reduced pressure and provides a force, which may be a compression force or lifting force, to the desired treatment area, e.g., treatment area 412. An interior surface member 440, which has a first surface 442 and a second, inward-facing surface 444, may be disposed between the patient's epidermis 414 and the dressing bolster 432. The second surface 436 of the dressing bolster 432 may be coupled, e.g., bonded or incorporated into, to the first surface 442 of the interior surface member 440. The interior surface member 440 may be independent of the dressing bolster 432. The interior surface member 440 may be fluid permeable or impermeable and may provide a barrier between the dressing bolster 432 and the patient's epidermis. In one illustrative embodiment, the interior surface member 440 avoid skin irritation that might result from the dressing bolster 432 interfacing with the patient's skin and facilitates removal sweat and other fluids at the surface using reduced pressure.

The dressing bolster 432 may be made from any of the bolster materials described elsewhere in this application. The dressing bolster 432 may include bolster material that is not uniform throughout since one may want the dressing bolster 432 to be more rigid (and not provide as much lift) in some places or one may want the dressing bolster 432 to be less rigid and to develop maximum lift in some places, e.g., like at the breasts on the brassiere embodiment below. The bolster material may be made more or less rigid using a bolster material with varying properties or using two or more different materials that are combined to form the bolster material. In some applications, it may be desirable to form the bolster material from a honeycomb material such as a Supracor® fusion-bonded honeycomb material from Supracor Systems, Inc. of Sunnyvale, California.

The dressing assembly 430 may further include an exterior surface member 446, or exterior member, which has a first side 448 and a second side 450. The interior surface member 440, or interior member, and the exterior surface member 446 may be made with a pre-tensioned elastic material such as a spandex material; for example, a Lycra® brand material might be used. The interior surface member 440 has high contractibility to avoid wrinkling, which would result in contact loading against the skin. Furthermore, the low friction of the material used for the inner surface member 440 helps to reduce the possibility of shear injury to the epidermis. Moreover, the permeability of the inner surface member 440, or layer, results in reduced-pressure transmission to the tissue site and provides a pathway for exudate removal. The interior surface member 440, or interior member, and the exterior surface member 446 may be coupled to form an envelope surrounding the dressing bolster 432.

The second side 450 of the exterior surface member 446 may be coupled to the first surface 434 of the dressing bolster 432. The coupling of the various members (e.g., surface 436 to surface 442 and surface 450 to 434) may occur in many ways; a number of examples follow. One might use adhesives such as acrylic adhesive, silicone adhesive, hydrogel, hydrocolloid, etc. or might use bonding such as heat bonding, ultrasonic bonding, or radio frequency bonding, etc. The coupling may occur in patterns or may cover the whole. Structural members may be added to the coupling to make the member behave anisotropically in a desired direction. In addition, struts or other mechanical elements may be supplied within the bolster to change the compression and characteristics of the dressing bolster 432.

The dressing assembly 430 is shown in FIGS. 6 through 8 with a substantially rectangular cross-section, but other shapes may be utilized to provide more of a vertical lifting force (vertical for the orientation shown in FIGS. 6 and 7). While the dressing bolster 432 is shown as an integral member, the dressing bolster 432 may also be formed with different sections of bolster material, each having distinct supplies of reduced-pressure, and may even have a section with positive pressure. Concerning the latter, one or more sealed chambers may be added to which a positive pressure could be provided to help redistribute loading or to add structural elements.

The dressing bolster 432 and any additional layers such as the interior surface member 440 and the exterior surface member 446 may be covered with an over-drape 462, which is part of a sealing subsystem 460. The over-drape 462 may extend beyond peripheral edges 438 and 439 to form drape extension 464, which has a first side 466 and a second side 468. A fluid seal may be formed between the drape extension 464 and the patient's epidermis 414 by using a sealing apparatus 469, such as a sealing tape, or drape tape 471, an adhesive (see adhesive 5 in FIG. 1), paste, hydrocolloid, hydrogel, or other sealing means. The drape tape 471 includes an adhesive 473. In some applications, a gasket material might be added between the epidermis 414 and the dressing bolster 432 or the over-drape 462. In another embodiment, the over-drape 462 may be applied only on the first side of the dressing bolster 432, and then a wide drape tape used to seal the edges, or peripheral portion, of the dressing bolster 432 with or without extensions 464.

The sealing subsystem 460 provides a fluid seal, or otherwise allows the system 410 to maintain reduced pressure at the desired treatment site 412. The sealing subsystem 460 preferably includes the over-drape 462 and the sealing apparatus 469. While described as forming a fluid seal, there may in fact be some leakage and the resultant small air leaks actually provide a low velocity airflow throughout the dressing assembly 430 that is distributed and helps to remove moisture. In an alternative embodiment, instead of using the over-drape 462, the exterior surface member 446 may be made to have an airtight exterior portion and drape tape may be directed to cover the edges of the bolster material as well an other portions that are not otherwise sealed.

A reduced-pressure subsystem 480 is shown in part and is analogous to the reduced-pressure subsystems of previously presented embodiments, e.g., 80 of FIG. 2. The reduced-pressure subsystem 480 includes a reduced-pressure interface 492, such as elbow port 494, that allows the reduced-pressure source to deliver reduced pressure through a reduced-pressure conduit 479 into the dressing assembly 430 and, in particular, into the dressing bolster 432. The reduced-pressure subsystem 480 may be controlled so as to vary the pressure to provide a constant level of compression as the patient's size changes due to edema decreasing. The reduced-pressure source may supply a constant reduced pressure or a variable reduced pressure. As with other embodiments described above, the reduced-pressure source may take many different forms including those mentioned elsewhere herein.

As shown clearly in FIG. 7, the dressing assembly 430 may include a transition area 452 on a portion of the dressing bolster 432. The transition area 452 may be tapered or otherwise shaped to reduce the thickness and increase flexibility and maximize shear compliance at the borders. This may help to distribute any concentrated shear loads such as those caused by contraction of the dressing assembly 430, patient mobility, and load concentrations caused by the discontinuity of stiffness between the dressing/splinted areas and the unsupported dermis. The transition area 452 may transition to one or more connection pieces 454, or joining elements 454.

A portion of the joining elements 454 may include fasteners 456, which may be a hook and loop fastener, clasps, or other means of connecting two portions of the joining elements 454. The joining elements 454 and fasteners 456 form a circumferential connector and with the dressing assembly 430 complete a path around the curved body part or form a completed, releasable circumferential member 458. Thus, the releasable circumferential member 458 extends around the patient's torso 404 to allow the releasable circumferential member 458 to be held against the torso 404 and, in particular, holds bolster 432 against the desired treatment area 412 even before the reduced pressure is delivered by the reduced-pressure subsystem 480. Additional drape tape may be used to provide a fluid seal over the joining elements 454 and fasteners 456.

The transition area 452 may include a first end 453 and a second end 455 of the dressing assembly 430 and in particular the ends of a longitudinal portion 457 that is shown surrounding the patient's torso 404. The two ends are thus brought together and releasably held by the releasable circumferential member 458, which includes the joining elements 454 and fasteners 456.

Figure 9:
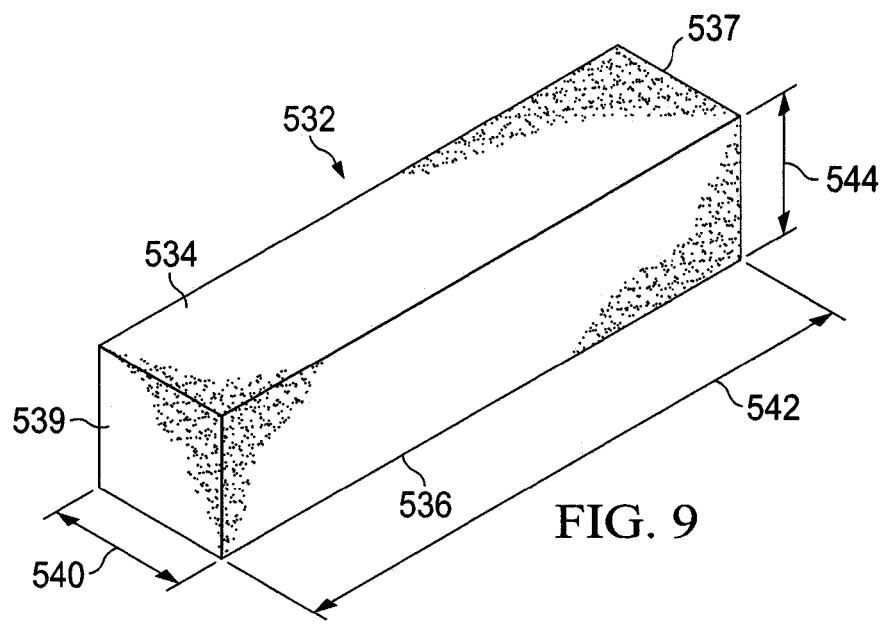
FIG. 9 is a schematic perspective view showing a bolster material.

The differences in surface areas of the first surface 434 and second surface 436 of the dressing bolster 432 contributes to the production of a net compressive (inward) force. The net compressive force increases linearly with the increase in the ratio of the circumference of the first surface 434 of the dressing bolster 432 to the second surface 436 of the dressing bolster 432. Thus, to have a greater compression developed, the dressing bolster 432 may be made thicker to increase the ratio. The bending stiffness of the dressing bolster 432 may also influence the delivery of the developed compression force. The net compressive force is distributed fairly uniformly if the dressing 430 has a low-bending stiffness. With reference briefly to FIG. 9, the low elastic stiffness along a second axis, which is parallel to 542, and the first axis, which is parallel to 540, contributes to reducing the bending stiffness of the dressing bolster 532.

Returning now to FIG. 6-8, in operation, the dressing assembly 430 is placed around the curved body part, e.g., the torso 404, of the patient with the dressing bolster 432 against the desired treatment area 412. The releasable circumferential connector 458 is utilized (i.e. joining elements 454 and fasteners 456 are activated) to form the completed releasable circumferential member. The reduced-pressure subsystem 480 may be activated so that the reduced-pressure subsystem 480 delivers reduced pressure to the sealing subsystem 460 causing the reduced pressure to be delivered to the dressing bolster 432. The dressing bolster 432 may then compress and collapse under the reduced pressure to deliver the support force to the desired treatment area 412. The support force may include a compressive force, which acts into the patient's torso and down into the epidermis 14, dermis 416, and down to subcutaneous levels 418 to the undermined subcutaneous tissue 420. The net compressive force for one segment is shown in FIG. 8 with reference numeral 424. A lateral force 426, i.e., toward peripheral edge 439, or lifting or upward force 426, may also be developed.

Referring now to FIG. 9, a portion of a dressing bolster 532 is shown which is made from an anisotropic material. One anisotropic material that may be used is AirX compression material, or fabric, available from the Tytex Group (www.tytex.com). The dressing bolster 532 has a first surface 534 and a second surface 536. It also has a top portion 537 which would be closest to the person's head for the embodiment shown in FIGS. 6 and 7, and a bottom portion 539 which would be closest to the person's feet for the embodiment shown in FIGS. 6 and 7. For description purposes, the dressing bolster 532 has three axes that are parallel to reference lines 540, 542, and 544, respectively. The material of the dressing bolster 532 is potentially anisotropic, which means that it will have different mechanical properties along different axes. For example, the compressive modulus may differ between at least two of the first, second, and third axes. In one illustrative embodiment, when it is desirable to provide an enhanced force, an anisotropic material may be selected and oriented to extend or to contract preferentially along one or more axes. This may be particularly desirable in applying a similar system to breast tissue as will now be considered.

Referring to FIGS. 10-14, a system 610 for providing a support force to breast tissue is presented. The system 610 includes a therapeutic brassiere 612 to provide support to breast tissue 614 in a breast area 616 on an upper portion of a patient's torso 604. Support may be provided in a defined support area 618 near or on the breast tissue 614, which may have been the subject of a surgical procedure, such as a partial or total mastectomy or a breast augmentation procedure. In the event of a mastectomy, the support area 618 may support remaining breast tissue.

The system 610 includes a dressing assembly 630, which includes a dressing bolster 632 having a first surface 634 and a second, inward-facing surface 636. The dressing assembly 630 may include an interior surface member 638 having a first surface 640 and a second, inward-facing surface 642. The interior surface member 638 may be coupled on a first surface 640 to the second surface 636 of the dressing bolster 632. The dressing assembly 630 may also include an exterior surface member 644, which has a first surface 646 and a second, inward-facing surface 648. The exterior surface member 644 may be coupled on a second surface to the first surface 634 of the bolster 632.

A sealing subsystem 660 provides a fluid seal sufficient to maintain a reduced pressure against the patient's epidermis in the desired support area 618 when under a reduced pressure from a reduced-pressure subsystem 680. The sealing subsystem 660 may take a number of different forms. The present embodiment includes an over-drape 662 that covers the dressing bolster 632 and may extend beyond peripheral edges 650 of the dressing bolster 632 to form extensions 664 to which a sealing apparatus 667 may be applied to form the fluid seal with the epidermis. The sealing apparatus 667 may take numerous forms such as adhesive, a sealing tape 668 or strip, double-sided sealing tape, paste, hydrocolloid, hydrogel, or other sealing means. The sealing apparatus 667 might also involve additional elements as shown in FIG. 13.

Figure 13:
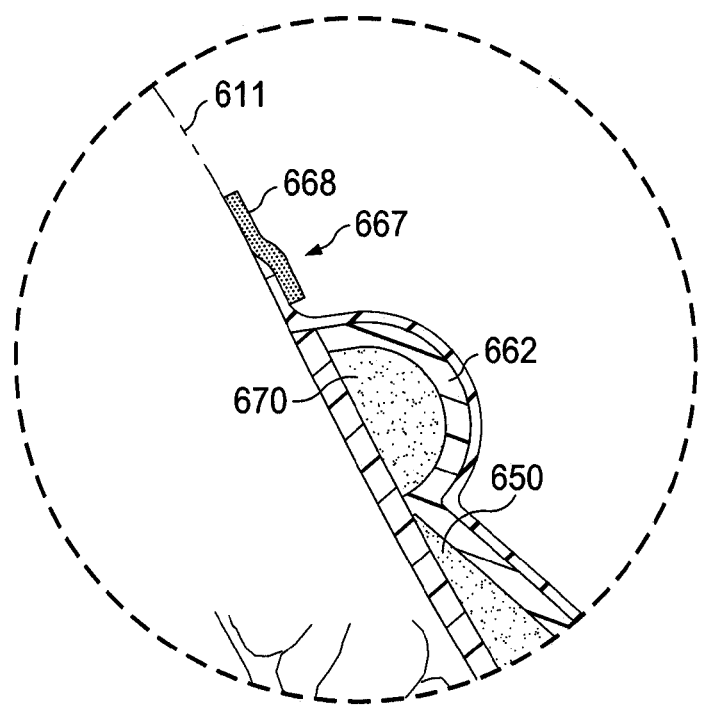
FIG. 13 is a schematic cross-section of a portion of the brassiere of FIGS. 10-12.

Referring now to FIG. 13, a closing apparatus 667 may simply be a tape 668 or an adhesive as previously mentioned or may further include a sealing bolster 670 which may be under more tension than the dressing bolster 632. The sealing bolster 670 has a portion of the over-drape 662 over the sealing bolster 670 and may form a compartment to which reduced-pressure subsystem 680 delivers reduced pressure or may be fluidly connected to the dressing bolster 632 to receive reduced pressure from the reduced-pressure subsystem 680.

Figure 14:
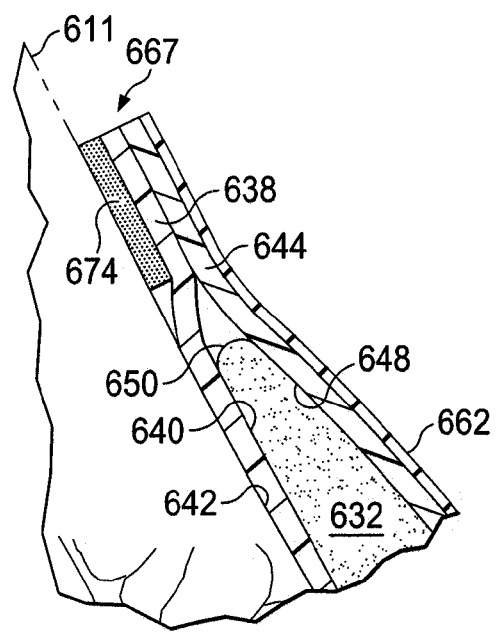
FIG. 14 is a schematic cross section of a portion of the brassiere of FIGS. 10-12 showing an illustrative, alternative aspect.

Referring now to FIG. 14, an illustrative, alternative embodiment of sealing apparatus 667 is presented. In this embodiment, the exterior surface member 644 and interior surface member 638 are placed adjacent to one another beyond the peripheral edge 650. The second surface 648 of the exterior surface member 644 and the first surface 640 of the interior surface member 638 may be coupled to one another by any known means. The members may be coupled in many different ways including one of the following: using adhesives such as by acrylic adhesive, silicone adhesive, hydrogel, hydrocolloid, etc; bonded by heating bonding, ultrasonic bonding, and radio frequency bonding, etc.; or other means. The coupling may occur in patterns or more completely. Structure might be added to the bond to make the material behave anisotropically in a desired direction. The embodiment in FIG. 14 shows an adhesive strip 674 applied between the second surface 642 of the interior surface member 638 and the patient's epidermis 611. Before the adhesive strip 674 is applied against the epidermis 611, the adhesive strip 674 may be covered with a removable backing or strip.

Figure 10:
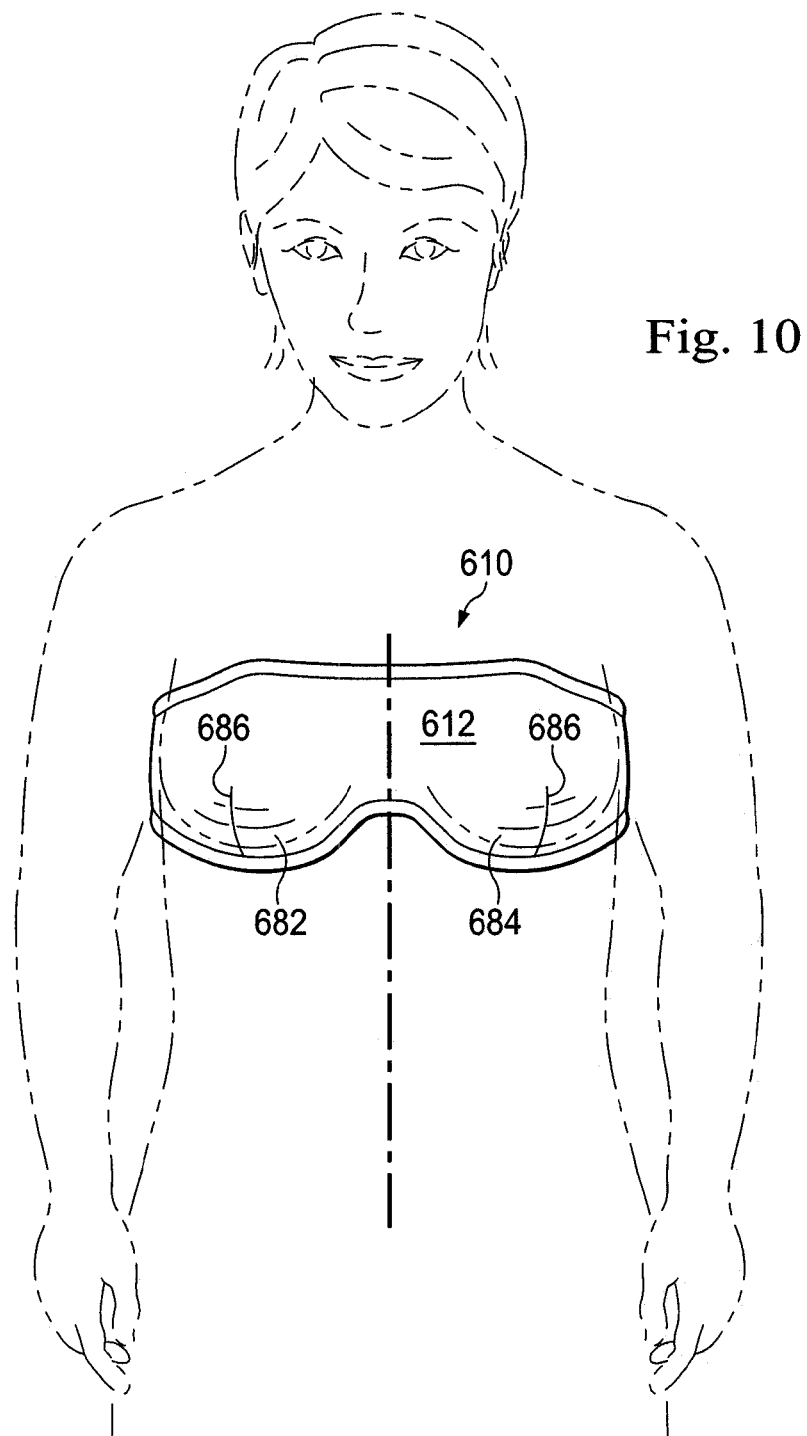
FIG. 10 is an anterior, schematic, perspective view of an illustrative embodiment of a brassiere for providing support to breast tissue.
Figure 11:
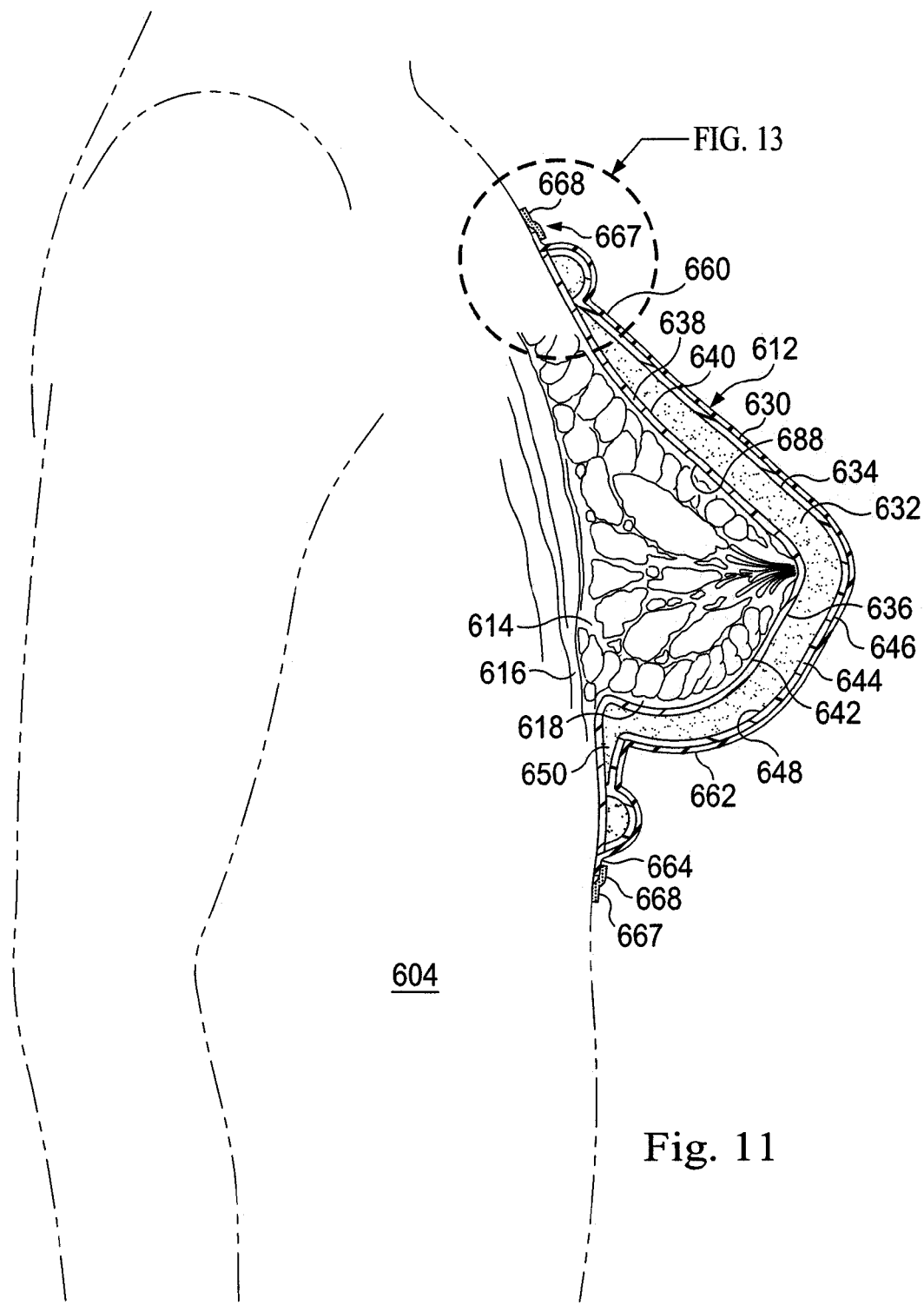
FIG. 11 is a cross section of the brassiere of FIG. 10 taken from one side.
Figure 12:
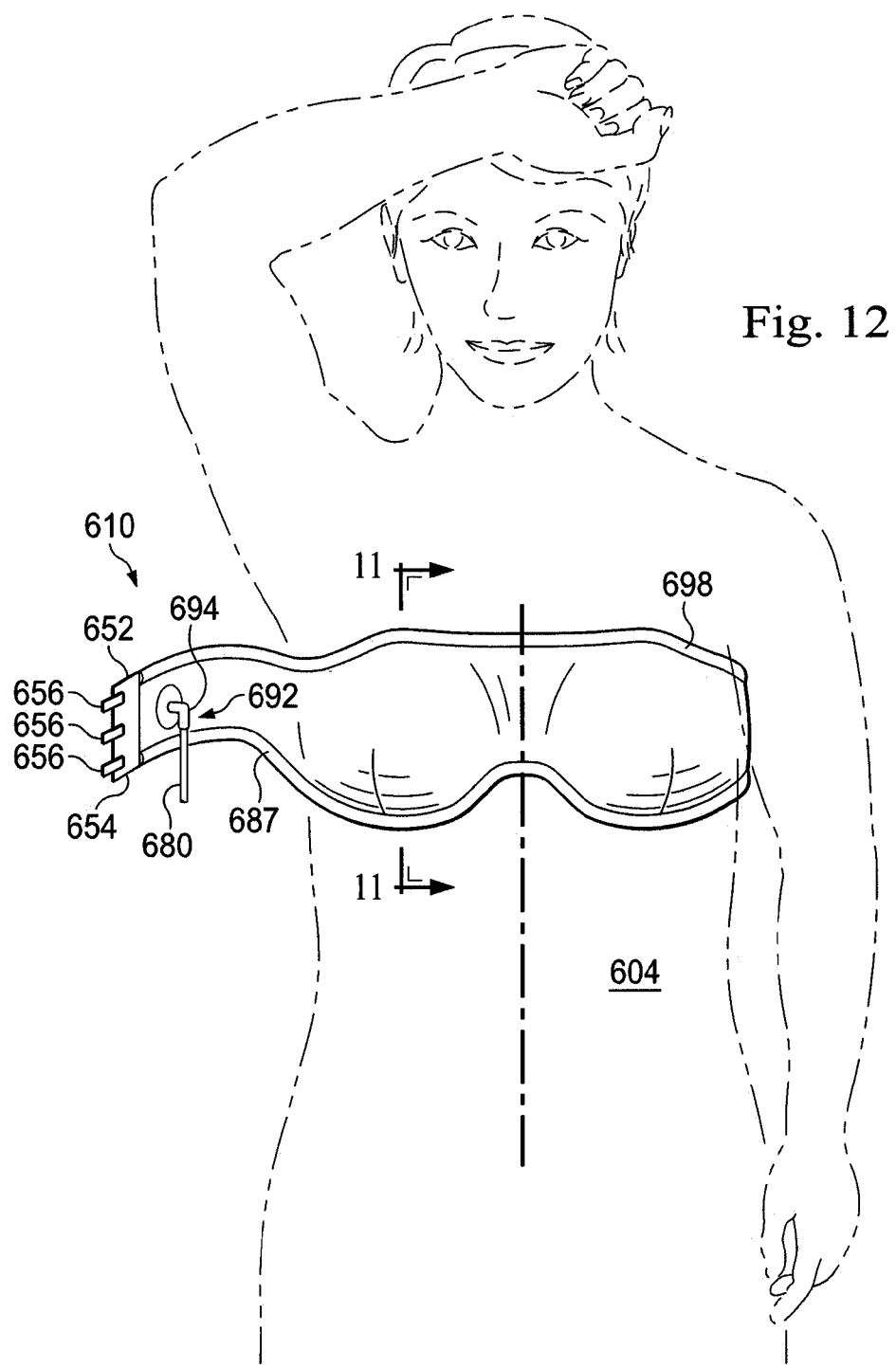
FIG. 12 is an anterior, schematic, perspective view of the brassiere of FIGS. 10-11 with a portion of the brassiere released to show a back portion of the brassiere.

Referring now primarily to FIGS. 10-12, support forces delivered to the support area 618 will now be explained in terms of the therapeutic brassiere 612. The brassiere 612 is formed as previously described in connection with the dressing assembly 630 and includes a first breast cup 682 and a second breast cup 684. In forming the breast cups 682 and 684 it may be necessary to add one or more seams 686. Each breast cup 682, 684 forms a pocket, such as pocket 688 shown in FIG. 11. The pocket 688 is for receiving breast tissue 614, or in the case of a mastectomy, may receive a temporary, post-surgical prosthetic, such as a silicon gel insert covered with a super absorbent material for assisting in the process of collecting exudates and helping to apply pressure to an underlying wound. In an alternative embodiment, a single cup may be formed that covers both breasts or more generally a portion of the patient's chest.

The therapeutic brassiere 612 might be bifurcated to have separate bolsters with separate sealing subsystems for each breast cup 682, 684 so that different pressure levels can be supplied to each breast cup 682, 684 to accommodate different sizes or situations. For example, if one breast has been the subject of a mastectomy and the other has not, different reduced pressures may be desired.

Referring now primarily to FIG. 12, the therapeutic brassiere 612 may have a transition area 652 that includes a joining element 654. The joining element 654 may be a web material and one or more fasteners 656, which couple with a receiving fastener on the opposite transition area 652 (not explicitly shown, but analogous to fastener 456 in FIG. 7). The fasteners 656 may be hook and loop members, zipper members, snaps, or other means. It may be desirable in some situations to apply drape tape over the top of the fasteners 456 to provide an adequate fluid seal. The reduced-pressure subsystem 680, which is only shown in part, delivers a reduced pressure through a reduced-pressure conduit 687, which is in fluid communication with the dressing bolster 632 through a reduced-pressure interface 692, such as an elbow port 694.

In operation, the system 610 is utilized by placing the therapeutic brassiere 612 on the torso 604 so that at least a portion of the bolster 632 is proximate the breast tissue 614, and preferably proximate the support area 618. The dressing assembly 630 along with the joining element 654 and fasteners 656 form a releasable circumferential connector 698 that holds the therapeutic brassiere 612 in place even before the reduced pressure from the reduced-pressure subsystem 680 is applied. Once the therapeutic brassier 612 is in place, the reduced-pressure subsystem 680 is activated and reduced pressure is delivered through the reduced-pressure interface 692 to the dressing bolster 632. The dressing bolster 632 collapses and contracts under the influence of the reduced pressure and thereby causes tension to develop throughout the circumferential connector 698 and provides a compression force and an element of a supporting (upward) force to the support area 618 or to the breast tissue 614.

The systems and apparatuses have been shown applied on various body parts, e.g., abdomen and breast, but other applications are included. For example, the system may be used on a thigh of a person in which case the bolster assembly might be held in place by a pair of shorts similar to biking shorts. As another example, the systems and apparatuses described for breast tissue might be modified to form a large single front cup that could be used to lift and support a pannus or other hanging flap of tissue. As still one more example, a reduced-pressure cup made in a analogous style to that presented for the breast tissue could be used for testicular support after surgery and might be incorporated into shorts.

According to another illustrative embodiment, a method of providing a force to at least a portion of a curved body part of a person includes the step of deploying a dressing assembly on the curved body part. The dressing assembly includes an interior surface member for placing over the desired treatment area and having a first surface and a second, inward-facing surface. The dressing bolster has a first surface and a second, inward-facing surface. The second, inward-facing surface of the dressing bolster is disposed against the first surface of the interior surface member. The dressing assembly may be sealed to the curved body part. The method further includes providing reduced pressure to the dressing assembly. When reduced pressure is applied, the dressing bolster goes from a first volume ($V_1$) at ambient pressure to a second volume ($V_2$) at reduced pressure. In other words, the first volume is greater than the second: $V_1 > V_2$. As the volume changes, a directed force is developed that may include a compressive portion, a lifting portion, or a inward closing portion.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A system for treating a curved body part on a patient, comprising:
   a dressing assembly shaped and configured to form a pocket to receive at least a portion of the curved body part, the dressing assembly including:
      an interior surface member having a first surface and a second, inward-facing surface, and
      a dressing bolster having a first surface and a second, inward-facing surface, wherein the second, inward-facing surface of the dressing bolster is disposed against the first surface of the interior surface member; and
   an over-drape configured to extend over the dressing assembly.

2. The system of claim 1, wherein the curved body part comprises breast tissue.

3. The system of claim 1, wherein the dressing bolster is a shaped dressing bolster configured to conform to the curved body part.

4. The system of claim 3, wherein the shaped dressing bolster comprises a peripheral edge including a chamfer, taper, or arcuate shape.

5. The system of claim 1, further comprising:
   a gasket material configured to be positioned between a portion of the dressing bolster and an epidermis of the patient; and
   a sealing apparatus configured to provide a seal between the over-drape and the epidermis.

6. The system of claim 1, wherein the dressing bolster is formed from a bolster material having a density greater than 25 kg/m$^3$.

7. The system of claim 1, wherein the dressing assembly further comprises an exterior surface member having a first surface and a second, inward-facing surface, wherein the second, inward-facing surface of the exterior surface member is disposed against the first surface of the dressing bolster.

8. The system of claim 1, wherein the dressing bolster comprises an anisotropic bolster material having a first, second, and third axes, and wherein compressive modulus differ between at least two of the first, second, and third axes.

9. The system of claim 1, wherein the interior surface member comprises an elastic material.

10. The system of claim 1, wherein the dressing assembly comprises:
an exterior surface member having a first surface and a second, inward-facing surface, wherein the second, inward-facing surface of the exterior surface member is disposed against the first surface of the dressing bolster; and
wherein the exterior surface member comprises an elastic material.

11. The system of claim 1, wherein the dressing assembly further comprises:
an exterior surface member having a first surface and a second, inward-facing surface, wherein the second, inward-facing surface of the exterior surface member is coupled to the first surface of the dressing bolster.

12. The system of claim 1, wherein the dressing assembly further comprises:
a longitudinal portion with a first end and a second end; and
a releaseable connector coupled to the first end and second end of the dressing assembly and adapted to releasably couple the first end of the dressing assembly to the second end of the dressing assembly.

13. The system of claim 12, wherein the releaseable connector comprises: a joining element and a releasable fastener.

14. The system of claim 1, further comprising a reduced-pressure subsystem for providing a reduced pressure to the dressing assembly, wherein the reduced-pressure subsystem comprises:
a reduced-pressure source for providing reduced pressure;
a reduced-pressure interface configured to be coupled to the over-drape;
a reduced-pressure delivery conduit for providing reduced pressure from the reduced-pressure source to the reduced-pressure interface.

15. The system of claim 1, wherein the dressing assembly is operable to generate a directed force under reduced pressure.

16. The system of claim 1, wherein the dressing assembly is operable to generate a lifting force under reduced pressure.

17. The system of claim 1, further comprising a releasable connector for holding the dressing assembly against the patient, wherein the releaseable connector comprises a joining element and a releasable fastener.

18. The system of claim 1, wherein the dressing bolster comprises an anisotropic bolster material having a first, second, and third axes, and wherein tension applied on the first axis causes a greater than 1:1 response of the anisotropic bolster material along the second axis.

19. A method for treating a curved body part of a patient using the dressing assembly of claim 1, comprising:
conforming the dressing assembly around the curved body part to form the pocket;
inserting a at least a portion of the curved body part into the pocket;
fluidly coupling a reduced-pressure source to the dressing assembly; and
activating the reduced pressure source to provide reduced pressure to the dressing assembly, whereby the dressing assembly contracts to form a directed force.

20. The method of claim 19, wherein the dressing assembly comprises a dressing bolster formed from a bolster material having a density greater than 25 kg/m3.

21. The method of claim 19, wherein the dressing assembly comprises a dressing bolster formed from a bolster material having a density less than a density of an epidermis of the patient, and wherein the directed force is a lifting force.

* * * * *